(12) United States Patent
Hays et al.

(10) Patent No.: US 7,359,536 B2
(45) Date of Patent: *Apr. 15, 2008

(54) AUTOMATED METHOD FOR IMAGE ANALYSIS OF RESIDUAL PROTEIN

(75) Inventors: Presley Hays, Pasadena, CA (US); Michal L. Peri, Irvine, CA (US); Douglas Harrington, San Clemente, CA (US)

(73) Assignee: Carl Zeiss MicroImaging AIS, Inc., Thornwood, NY (US)

( * ) Notice: Subject to any disclaimer, the term of this patent is extended or adjusted under 35 U.S.C. 154(b) by 705 days.

This patent is subject to a terminal disclaimer.

(21) Appl. No.: 10/728,698

(22) Filed: Dec. 5, 2003

(65) Prior Publication Data
US 2004/0120562 A1    Jun. 24, 2004

Related U.S. Application Data

(63) Continuation of application No. 10/014,006, filed on Dec. 10, 2001, now Pat. No. 6,671,393, and a continuation-in-part of application No. 08/758,436, filed on Nov. 27, 1996, now Pat. No. 6,215,892.

(60) Provisional application No. 60/026,805, filed on Nov. 30, 1995.

(51) Int. Cl.
*G06K 9/00* (2006.01)

(52) U.S. Cl. .................... 382/128; 382/308

(58) Field of Classification Search ........ 382/128–134, 382/260, 264, 274, 275, 276, 308; 536/24.31; 435/6; 345/591, 604
See application file for complete search history.

(56) References Cited

U.S. PATENT DOCUMENTS

| 3,824,393 A | 7/1974 | Brain |
| 3,851,972 A | 12/1974 | Smith et al. |
| 4,011,004 A | 3/1977 | Levine et al. |
| 4,125,828 A | 11/1978 | Resnick et al. .......... 340/146.3 |
| 4,196,265 A | 4/1980 | Koprowski et al. |
| 4,249,825 A | 2/1981 | Shapiro |
| 4,342,905 A | 8/1982 | Fujii et al. |
| 4,393,466 A | 7/1983 | Deindoerfer et al. |

(Continued)

FOREIGN PATENT DOCUMENTS

DE    3340647    5/1985

(Continued)

OTHER PUBLICATIONS

Ballard, D.H., et al. "Computer Vision" *Prentice-Hall, Inc.*, Englewood Cliffs, NJ 07632 pp. 65-70 and 149-165 (1982).
Bander, N.H., "Monoclonal Antibodies to Renal Cancer Antigens", vol. 18, Supp. 2, pp. 10-12, 1990. Abstract.
Duda R.O., et al. "Pattern Classification and Scene Analysis" *J. Wiley & Sons, Inc.* pp. 228-239 and 276-284 (1973).
McKeough et al., "A Low-Cost Automatic Translation and Autofocusing Systems for a Microscope", *Measurement Science and Technology, IOP Publishing*, Bristol, GB, vol. 6, No. 5, pp. 583-587, May 1, 2995.

(Continued)

*Primary Examiner*—Kanjibhai Patel
(74) *Attorney, Agent, or Firm*—Patterson, Thuente, Skaar & Christensen, P.A.

(57) ABSTRACT

An automated method for evaluating the amount of residual protein levels following treatment of cellular specimens. Particular methods include the measurement of maternal neutrophil alkaline phosphatase after treatment with or without urea or heat, measurement of leukocyte acid phosphatase after treatment with or without tartrate, and measurement of leukocyte esterase after treatment with α-naphthol butyrate with or without fluoride.

12 Claims, 25 Drawing Sheets

U.S. PATENT DOCUMENTS

| | | |
|---|---|---|
| 4,513,438 A | 4/1985 | Graham et al. |
| 4,612,614 A | 9/1986 | Deindoerfer et al. |
| 4,656,594 A | 4/1987 | Ledley |
| 4,673,973 A | 6/1987 | Ledley |
| 4,700,298 A | 10/1987 | Palcic et al. |
| 4,741,043 A | 4/1988 | Bacus |
| 4,939,240 A | 7/1990 | Chu et al. .................. 530/387 |
| 4,945,220 A | 7/1990 | Mallory et al. |
| 4,965,725 A | 10/1990 | Rutenberg |
| 4,991,223 A | 2/1991 | Bradley |
| 5,003,165 A | 3/1991 | Sarfati et al. |
| 5,008,185 A | 4/1991 | Bacus |
| 5,016,173 A | 5/1991 | Kenet et al. ........... 364/413.13 |
| 5,018,209 A | 5/1991 | Bacus |
| 5,051,816 A | 9/1991 | Harrison et al. |
| 5,068,909 A | 11/1991 | Rutherford et al. |
| 5,085,325 A | 2/1992 | Jones et al. |
| 5,087,965 A | 2/1992 | Torre-Bueno |
| 5,123,055 A | 6/1992 | Kasdan |
| 5,202,931 A | 4/1993 | Bacus |
| 5,231,580 A | 7/1993 | Cheung et al. ........ 364/413.13 |
| 5,233,684 A | 8/1993 | Ulichney et al. |
| 5,254,845 A | 10/1993 | Burgess et al. |
| 5,257,182 A | 10/1993 | Luck et al. |
| 5,268,966 A | 12/1993 | Kasdan |
| 5,287,272 A | 2/1994 | Rutenberg et al. |
| 5,317,140 A | 5/1994 | Dunthorn |
| 5,321,545 A | 6/1994 | Bisconte |
| 5,333,207 A | 7/1994 | Rutenberg |
| 5,338,924 A | 8/1994 | Barrett et al. |
| 5,352,613 A | 10/1994 | Tafas et al. |
| 5,375,177 A | 12/1994 | Vaidanathan et al. |
| 5,409,007 A | 4/1995 | Saunders et al. |
| 5,428,690 A | 6/1995 | Bacus et al. ................ 382/128 |
| 5,432,871 A | 7/1995 | Novik |
| 5,449,622 A | 9/1995 | Yabe et al. |
| 5,459,384 A | 10/1995 | Engelse et al. |
| 5,463,470 A | 10/1995 | Terashita et al. |
| 5,469,353 A | 11/1995 | Pinsky et al. |
| 5,473,706 A | 12/1995 | Bacus et al. |
| 5,481,401 A | 1/1996 | Kita et al. |
| 5,499,097 A | 3/1996 | Ortyn et al. |
| 5,515,172 A | 5/1996 | Shiau |
| 5,526,258 A | 6/1996 | Bacus |
| 5,533,628 A | 7/1996 | Tao |
| 5,583,666 A | 12/1996 | Ellson et al. |
| 5,585,469 A | 12/1996 | Kojima et al. |
| 5,602,941 A | 2/1997 | Charles et al. |
| 5,625,705 A | 4/1997 | Recht |
| 5,635,402 A | 6/1997 | Alfano et al. |
| 5,646,677 A | 7/1997 | Reber |
| 5,647,025 A | 7/1997 | Frost et al. |
| 5,671,288 A | 9/1997 | Wilhelm et al. |
| 5,690,892 A | 11/1997 | Babler et al. |
| 5,691,779 A | 11/1997 | Yamashita et al. |
| 5,701,172 A | 12/1997 | Azzay |
| 5,706,093 A | 1/1998 | Komiya |
| 5,726,009 A | 3/1998 | Connors et al. |
| 5,735,387 A | 4/1998 | Polaniec et al. |
| 5,740,267 A | 4/1998 | Echerer et al. |
| 5,740,270 A | 4/1998 | Rutenberg et al. |
| 5,783,814 A | 7/1998 | Fairley et al. |
| 5,799,105 A | 8/1998 | Tao |
| 5,846,749 A | 12/1998 | Slamon et al. |
| 5,851,186 A | 12/1998 | Wood et al. |
| 5,854,851 A | 12/1998 | Bamberger et al. |
| 5,867,598 A | 2/1999 | de Queiroz |
| 5,877,161 A | 3/1999 | Riabowol |
| 5,880,473 A | 3/1999 | Ginestet |
| 5,888,742 A | 3/1999 | Lal et al. |
| 5,889,881 A | 3/1999 | Macaulay et al. |
| 5,911,003 A | 6/1999 | Sones |
| 5,911,327 A | 6/1999 | Tanaka et al. |
| 5,966,309 A | 10/1999 | O'Bryan et al. |
| 5,966,465 A | 10/1999 | Keith et al. |
| 6,006,191 A | 12/1999 | DiRienzo |
| 6,007,996 A | 12/1999 | McNamara et al. |
| 6,011,595 A | 1/2000 | Henderson et al. |
| 6,031,929 A | 2/2000 | Maitz et al. |
| 6,040,139 A | 3/2000 | Bova ........................... 435/6 |
| 6,058,322 A | 5/2000 | Nishikawa et al. |
| 6,069,242 A | 5/2000 | Zavada et al. ........... 536/24.31 |
| 6,072,570 A | 6/2000 | Chipman et al. |
| 6,097,838 A | 8/2000 | Klassen et al. |
| 6,101,265 A | 8/2000 | Bacus et al. |
| 6,117,985 A | 9/2000 | Thomas et al. |
| 6,122,400 A | 9/2000 | Reitmeier |
| 6,125,194 A | 9/2000 | Yeh et al. |
| 6,141,602 A | 10/2000 | Igarashi et al. |
| 6,151,535 A | 11/2000 | Ehlers |
| 6,169,816 B1 | 1/2001 | Ravkin |
| 6,215,892 B1 | 4/2001 | Douglass et al. |
| 6,215,894 B1 | 4/2001 | Zeleny et al. |
| 6,225,636 B1 | 5/2001 | Ginestet |
| 6,226,392 B1 | 5/2001 | Bacus et al. |
| 6,226,636 B1 | 5/2001 | Abdel-Mottalep et al. |
| 6,236,031 B1 | 5/2001 | Ueda |
| 6,238,892 B1 | 5/2001 | Mercken et al. |
| 6,259,807 B1 | 7/2001 | Ravkin |
| 6,281,874 B1 | 8/2001 | Sivan et al. |
| 6,290,907 B1 | 9/2001 | Takahasi et al. |
| 6,313,452 B1 | 11/2001 | Paragano et al. |
| 6,374,989 B1 | 4/2002 | Vany Dyke, Jr. et al. |
| 6,418,236 B1 | 7/2002 | Ellis et al. |
| 6,466,690 B2 | 10/2002 | Bacus et al. |
| 2002/0067409 A1 | 6/2002 | Hararai et al. |
| 2002/0164810 A1 | 11/2002 | Dukor et al. |
| 2003/0124589 A1 | 7/2003 | Piper |
| 2003/0170703 A1 | 9/2003 | Piper et al. |

FOREIGN PATENT DOCUMENTS

| | | |
|---|---|---|
| DE | 3735091 | 4/1998 |
| EP | 0213666 | 3/1987 |
| EP | 0557871 | 9/1993 |
| EP | 0713086 | 5/1996 |
| WO | 92/17848 | 10/1992 |
| WO | 97/20198 | 6/1997 |
| WO | 00/49391 | 8/2000 |
| WO | 01/37206 | 5/2001 |
| WO | 03/014795 | 2/2003 |

OTHER PUBLICATIONS

Roca et al., "New Autofocusing Algorithm for Cytological Tissue in a Microscopy Environment", *Optical Engineering, Soc. Of Photo-Optical Instrumentation Engineers*, Bellingham, US, vol. 37, No. 2, pp. 635-641, Feb. 1, 2998.

Press, Michael F. et al., "Her-2/nue Expression in Node-negative Breast Cancer: Direct Tissue Quantitation by Computerized Image Analysis and Association of Overexpression with Increased Risk of Recurrent Disease", Cancer Research 53, 4960-4970, Oct. 1993.

Diamond, David A. et al., "Computerized Image Analysis of Nuclear Shape as a Prognostic Factor for Prostatic Cancer", The Prostate 3:321-332 (1982).

Levine, Gary M. et al., "Quantitative Immunocytochemistry by Digital Image Analysis: Application to Toxicologic Pathology", XICOLOGIC Pathology ISSN:0192-6233, vol. 15, No. 3, pp. 303-307, 1987.

Enestrom, Sverker et al., "Quantitative Ultrastructural Immunocytochemistry Using a Computerized Image Analysis System", Stain Technology, vol. 65, No. 6, pp. 263-278, 1990.

John C. Russ, "Image Processing Handbook, 2nd Edition", Library Congress Cataloging-in-Publication Data, 1996.

ChromaVision, "Products", http://www/chromavision.com/products/index.htm.

Pratt, William K., "Digital Image Processing, 2$^{nd}$ Edition," A Wiley-Interscience Publication, 1991.

Castleman, Kenneth R., "Digital Image Processing", Library of Congress Cataloging-in-Publication Data, 1996.

Ledley, R.S. et al., "Fundamentals of True-Color Image Processing", IEEE, pp. 791-795, 1990.

Mize, R. Ranney et al., "Quantitative immunocytochemistry using an image analyzer. I. Hardware evaluation, image processing, and data analysis", Journal of Neuroscience Methods, 26 (1988) 1-24.

Caulet S. et al., "Comparative Quantitative Study of Ki-67 Antibody Staining in 78 B and T Cell Malignant Lymphoma (ML) Using Two Image Analyser Ssystems", Path. Res. Pract. 188, 490-496 (1992).

Goldschmidt, R.A. et al., "Automated Immunohistochemical Estrogen Receptor Staining and Computerized Image Analysis-Comparison with Biochemical Methods", Supplied by the British Library—"The world's knowledge" www.bl.uk.

Gross, Douglas S. et al., "Quantitative Immunocytochemistry of Hypothalamic and Pituitary Hormones: Validation of an Automated, Computerized Image Analysis System", The Journal of Histochemistry and Cytochemistry, vol. 33, No. 1, pp. 11-20, 1985.

Maudelonde, T. et al., "Immunostaining of Cathepsin D in Breast Cancer: Quantification by Computerised Image Analysis and Correlation with Cytosolic Assay", Eur T Cancer, vol. 28A, No. 10, pp. 1686-1691, 1992.

Aziz, Douglas C., "Quantitation of Estrogen and Progesterone Receptors by Immunocytochemical and Image Analyses", Anatomic Pathology, From Cytometrics, Inc., Division of Specialty Laboratories, pp. 105-111, Jul. 1991.

Unnerstall, James R. et al., "New Approaches to Quantitative Neuropathology: Multtivariate Analysis of Morphologic and Neurochemical Measures", Neurobiology of Aging, vol. 8, pp. 567-569, Pergamon Journals Ltd., 1987.

Schultz, Daniel S., et al., "Comparison of Visual and CAS-200 Quantitation of Immunocytochemical Staining in Breast Carcinoma Samples", Analytical and Quantitative Cytology and Histology, vol. 14, No. 1, Feb. 1992.

Horsfall, D.J. et al., "Immunocytochemical assay for oestrogen receptor in fine needle aspirates of breast cancer by video image analysis", Br. J. Cancer (1989), 59, 129-134.

McClelland, Richard A. et al., "Automated Quantitation of Immunocytochemically Localized Estrogen Receptors in Human Breast Cancer", Cancer Research 50, 3545-3550, Jun. 1990.

Baddoura, Fady K. et al., "Image Analysis for Quantitation of Estrogen Receptor in Formalin-Fixed Paraffin-Embedded Sections of Breast Carcinoma", Modern Pathology, vol. 4, No. 1, 1991, pp. 91-95.

Kerns, B.J. et al., "Estrogen receptor status evaluated in formalin-fixed paraffin embedded breast carcinomas determined by automated immunohistochemistry and image analysis", Proceedings of the American Association for Cancer Research, vol. 35, Mar. 1994.

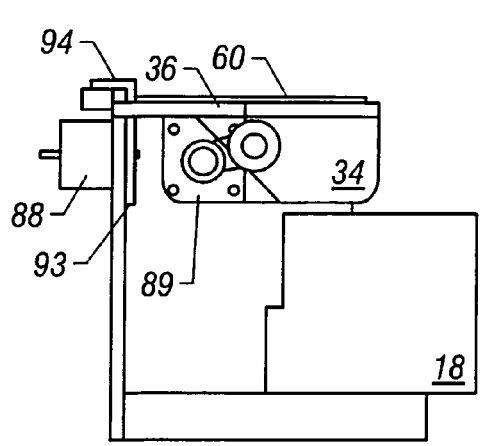
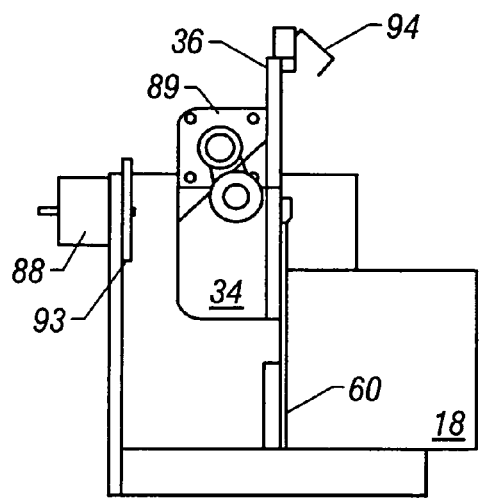
FIG. 9A          FIG. 9B
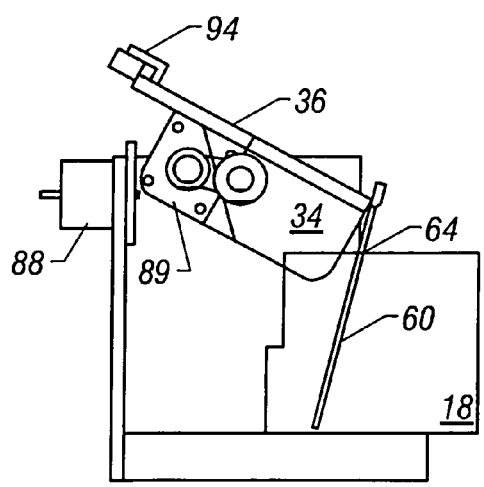
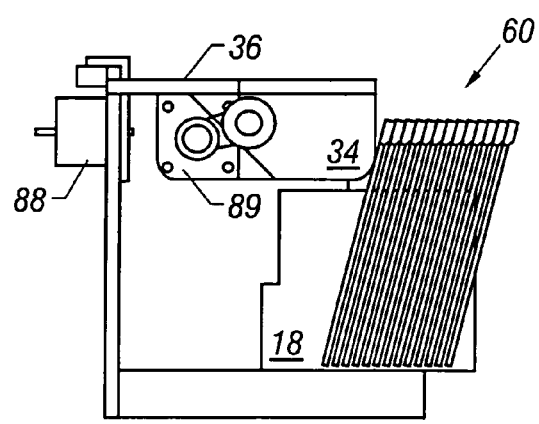
FIG. 9C          FIG. 9D

AUTOMATED METHOD FOR IMAGE ANALYSIS OF RESIDUAL PROTEIN

CLAIM OF PRIORITY

This application is a continuation of U.S. patent application Ser. No. 10/014,006, filed Dec. 10, 2001 now U.S. Pat. No. 6,671,393, which claims benefit of priority from U.S. patent application Ser. No. 09/612,022, filed Jul. 7, 2000 (now U.S. Pat. No. 6,330,349), which claims benefit of priority from U.S. Provisional Application No. 60/143,181, filed Jul. 9, 1999 and is a continuation-in-part of U.S. patent application Ser. No. 08/758,436, filed Nov. 27, 1996 (now U.S. Pat. No. 6,215,892), which claims the benefit of priority from U.S. Provisional Patent Application No. 60/026,805, filed Nov. 30, 1995, each of which is incorporated by reference in their entirety.

TECHNICAL FIELD

The invention relates generally to light microscopy and, more particularly, to automated analysis of cellular specimens containing stained markers.

BACKGROUND OF THE INVENTION

Alkaline phosphatase concentrations usually increase in blood neutrophils of normal pregnant women. However, the maternal neutrophil alkaline phosphatase (NAP) in Down's syndrome pregnancies (women with trisomy 21 fetuses) differs from NAP found in normal pregnancies. NAP from women with Down's syndrome pregnancies is characterized by: (1) an increase in NAP enzyme activity over that found in normal pregnancies, (2) NAP thermal stability, (2) NAP stability in urea, (3) a significant decrease in reactivity with anti-liver-type alkaline phosphatase (AP); (4) low reactivity with anti-placental-type AP or anti-intestinal-type AP antibodies; (5) altered response to AP enzyme inhibitors; and (6) marked dispersion of NAP lead citrate reaction products or anti-NAP antibody colloidal gold-labeling in neutrophil cytoplasm, as detected by electron microscopy. These characteristics suggest that neutrophils of a woman with a trisomy 21 fetus contain two AP isoenzymes: the liver/bone type AP and an a typical AP that is related to the early placental form. Thus, the non-specific alkaline phosphatase isoenzyme can be an "enzyme marker" to diagnose Down's syndrome pregnancies.

The histochemical measurement of maternal NAP has a high detection rate for the prenatal detection of Down's syndrome pregnancies. However, because the histochemical method is laborious and subjective to use, the method has not gained widespread acceptance in prenatal screening programs.

Some automated methods have been developed. Tafas et al. have developed an image analysis method for the measurement of neutrophil alkaline phosphatase (NAP) and established a correlation of urea-resistant fraction of NAP (URNAP)/NAP scoring between the manual and automated methods for prenatal screening of Down's syndrome (U.S. Pat. No. 5,352,613 to Tafas et al.; Tafas et al., *Fetal Diagn. Ther.* 11 (4):254-259, 1996). Measurements ("scores") obtained by manual and automated methods correlate, but the automated scoring is threefold faster. However, a less laborious and subjective automated image analysis method could have benefits in the medical arts.

SUMMARY OF THE INVENTION

The invention provides an automated method for the measurement of a residual component of a cellular protein. A specimen (sample) to be stained with a cytochemical stain is obtained from a subject. At least one subsample is treated before being stained, such that the treatment may affect the measurable protein level. At least one subsample is not treated, to serve as a control. The untreated subsample and the treated subsample are stained together, for uniformity of staining. An apparatus automatically selects a position in each subsample for candidate objects of interest and obtains a low magnification color digital image of the candidate objects of interest. The apparatus automatically filters the pixels of the candidate object of interest with a low pass filter and morphologically processes the candidate object of interest pixels to identify artifact pixels, identifying the candidate objects of interest from the remaining candidate object of interest pixels in the subsample not identified as artifact pixels. The apparatus is adjusted to high magnification for automatically acquiring a high magnification image of the subsample, at the location coordinates corresponding to the low magnification image, for each candidate object of interest. The apparatus automatically transforms pixels of the high magnification image in the first color space to a second color space to differentiate high magnification candidate objects of interest pixels from background pixels, identifying objects of interest from the candidate object of interest pixels in the second color space. The protein level is scored in the untreated and the treated subsamples. The value Delta ($\Delta$) is determined ($\Delta$=[protein level in the treated subsamples]/[protein level in the untreated subsamples]) as a measurement of the residual component of the cellular protein.

In particular embodiments, the method is for the measurement of maternal neutrophil alkaline phosphatase after treatment with or without urea or heat (diagnostic for Down's syndrome pregnancies), measurement of leukocyte acid phosphatase after treatment with or without tartrate (diagnostic for hairy cell leukemia), and measurement of leukocyte esterase after treatment with $\alpha$-naphthol butyrate with or without fluoride (diagnostic for leukemia).

BRIEF DESCRIPTION OF THE DRAWINGS

FIG. 6 shows a slide carrier. FIG. 6b is a bottom view of the slide carrier of FIG. 6a.

FIG. 7 shows views of an automated slide handling subsystem.

FIGS. 9a-9d illustrate the output operation of the automated slide handling subsystem.

FIG. 13 shows flow diagrams of procedures for determining a focal position.

FIG. 17 shows flow diagrams for processes to locate and identify objects of interest in a stained cellular specimen on a slide.

DETAILED DESCRIPTION

Principle

Figure 1:
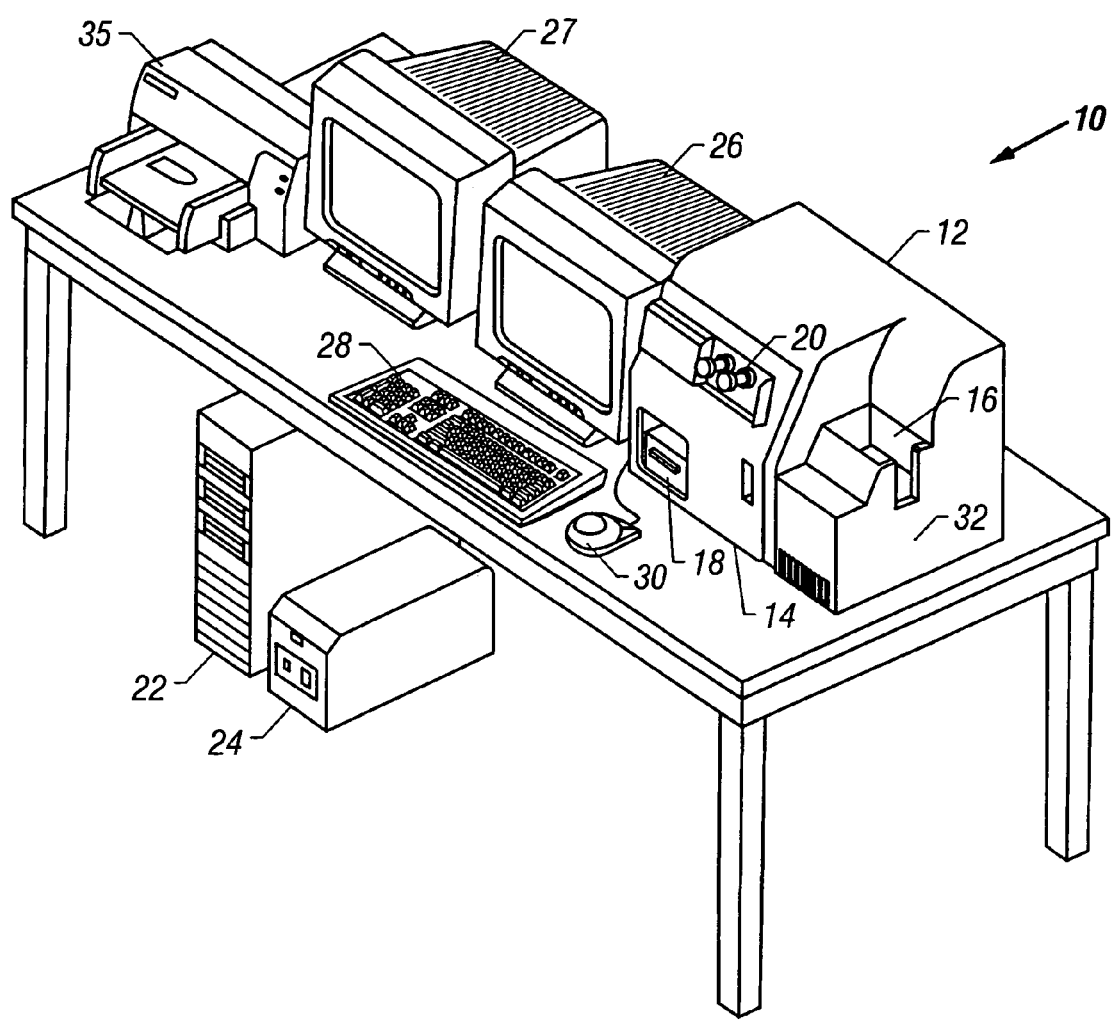
FIG. 1 is a perspective view of an apparatus for automated cell image analysis.

The invention provides an automated method cell image analysis which determines residual protein levels, in a greatly improved manner over manual scoring techniques. The invention provides a method ("the Delta method") of quantitating the residual protein remaining in a cell after a treatment of cells. The term "residual protein levels" refers to the measurable protein of interest remaining in a cell after the treatment; thus the term "residual protein" can refer either the actual protein remaining in the cell or the remaining protein activity, for example, the remaining enzyme activity. While current automated methods can eliminate the problem of laboratory-to-laboratory and technologist-to-technologist scoring variations through an objective imaging processing scoring technique, the problems caused by staining variations and individual patient "nominal" measurement ("score") variations cannot be eradicated by automation. However, by combining the scientific advantages of automation and the Delta method, as well as the greatly increased speed with which residual protein scores can be evaluated, the invention is a major improvement over methods currently available. The Delta method, as automated, has considerable diagnostic potential.

Continued dependence on manual input can lead to errors in image analysis. Additionally, manual methods can be extremely time consuming and can require a high degree of training to properly identify or quantify cells. The associated manual labor leads to a high cost for these procedures. A need exists, therefore, for an improved automated cell image analysis system which can quickly and accurately scan large amounts of biological material on a slide.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

All publications, patent applications, patents, and other references mentioned herein are incorporated by reference in their entirety. In case of conflict, the present application, including definitions, will control. In addition, the materials and methods described herein are illustrative only and not intended to be limiting. Other features and advantages of the invention will be apparent from the following detailed description, the drawings, and from the claims.

Delta Method

The Delta method is the measurement of a residual amount of cellular enzyme or protein following treatment of a cell. Various cellular treatments include acid, base, high salt, low salt, heat, an enzyme inhibitor (such as levamisole) or a detergent. A cellular specimen (a "sample") is split to provide two or more subsamples. In at least one subsample, the total protein is measured, or scored. In at least one other subsample, the residual protein levels present after treatment is scored. The residual protein is compared to the total protein score from a subsample obtained from the same specimen.

The terms "sample" and "subsample" include cellular material derived from a subject. Such samples include but are not limited to hair, skin samples, tissue sample, cultured cells, cultured cell media, and biological fluids. A tissue is a mass of connected cells (e.g., CNS tissue, neural tissue, eye tissue, placental tissue) derived from a human or other animal and includes the connecting material and the liquid material in association with the cells. A biological fluid is a liquid material derived from a human or other animal. Such biological fluids include but are not limited to blood, plasma, serum, serum derivatives, bile, phlegm, saliva, sweat, amniotic fluid, and cerebrospinal fluid (CSF), such as lumbar or ventricular CSF. The term "sample" also includes media containing isolated cells. The quantity of sample required to obtain a reaction may be determined by one skilled in the art by standard laboratory techniques. The optimal quantity of sample may be determined by serial dilution.

Current automated techniques do not allow for variations in either a patient's protein score that is unrelated to the condition being diagnosed or in a method used to calculate the protein score. Regarding variations in methods used for calculating protein scores, the absolute value of a patient's protein score depends crucially on the quality of specimen staining and the standards applied in scoring the individual specimen (which typically is subjective, varying from laboratory-to-laboratory and technologist-to-technologist). Hence, the score for a given slide, as compared to an absolute standard (as is currently typical in laboratory procedures) varies depending upon how that slide is stained and scored. This variation can be on the order of the difference expected between Down's pregnancies and normal pregnancies, meaning that an incorrect patient diagnosis becomes highly likely.

The Delta method compensates for the sources of variation by using the patient herself as a control, rather than using the statistical distributions derived from other patients as the control. This compensation is accomplished by preparing multiple subsample slides from the same specimen and then exposing subsamples to various treatments. An untreated subsample slide serves as the control. All of the subsample slides are then stained together as a batch and scored to determine the difference that the treatment causes in the protein scores for that particular patient.

The quantity "Delta" can be written as:

$$\Delta=[\text{protein level in the treated subsamples}]/[\text{protein level in the untreated subsamples}]$$

where the total protein level is determined from the untreated subsamples and the residual protein level is determined from the treated subsamples. A $\Delta$ value can indicate the presence of a condition of interest. By analyzing many cases, the ranges of $\Delta$'s indicative of a particular condition can be determined.

The advantages of the Delta method are several. First, the problem with variations in the individual patient and her "nominal" score is avoided because each patient is being judged against her own personal standard. The characteristics of this phenomenon are reflected in the statistical determination of what the different $\Delta$ ranges represent.

A second advantage of the Delta method is that the variability of scoring methods caused by inter-laboratory and inter-technologist biases is removed because the same scoring standard is applied to the test slides as to the control. The method preferably includes that the scoring of all slides from a patient be scored by the same technologist. Also, by staining the test slides in the same batch as the control, staining variations can be removed because any batch-specific or reagent lot-specific variation affects all the slides. In current standard methods, such variations result in an overall shift in the protein score of the test slides, which are then be compared to statistical results to result in an incorrect conclusion.

One problem with current automated systems is the difficulty in evaluating the amount of a marker present in a cellular specimen. (A "marker" may be any polypeptide sequence or feature of the protein that can be detected.) For example, a protein is stained to cause an insoluble product which identifies the marker to become colored, often red. A subsample can be counter-stained, for example with hematoxylin, to make the nuclei of the cells become blue in color. A pathologist viewing such a slide detects cells of interest by locating those cells having a nucleus of the color, shape, and size expected for a cell of interest. The pathologist subjectively evaluates the intensity of the red color for each located cell and assigns a score to each. The pathologist then subjectively determines whether the number of intensely red cells and moderately red cells are sufficient to determine a particular condition. According to that procedure, a pathologist sums the subjectively assigned ratings for marker identifying precipitate in the first 100 neutrophils to arrive at a score which may be used to determine the relative red intensity of the neutrophils in the cellular sample. This score is then used to determine whether the condition associated with the presence of the marker is indicated.

In one embodiment, the Delta method measures residual enzyme. In particular, the NAP Delta method measures maternal neutrophil alkaline phosphatase, for evaluating the likelihood that a pregnant woman is carrying a Down's syndrome fetus. Resistance to urea or heat exposure of NAP in the peripheral blood of a pregnant woman correlates with an increased risk of Down's syndrome incidence in the fetus. The resistance to urea or heat exposure is measured by comparing the NAP scores for urea-exposed or heat-exposed blood subsamples to NAP scores for untreated blood subsamples.

Current automated methods for measuring NAP do not allow for variations in the patient's particular NAP score, unrelated to the pregnancy. Pregnancy is known to lead to a significant increase in NAP score. But this NAP score is an increase from the woman's "nominal" NAP score before the pregnancy, so that a woman with a higher nominal NAP score should have a greater score when elevated due to pregnancy. The variation in nominal scores is, in the art, taken into account only in the mean, for a large number of patients, rather than for each individual patient.

The Delta method uses the patient herself as a control, not the statistical distributions. Multiple slides (subsamples) are prepared from the same specimen (sample). One slide can be exposed to urea, one slide can be exposed to heat, and one slide untreated. The untreated slide serves as the control. All of the slides are stained together as a batch. When the slides are scored, the difference that urea or heat exposure causes in the NAP scores for that patient can be examined. Alternatively, enzyme inhibitors of NAP can be used as the treatment. For example, alkaline phosphatase inhbitors such as levamisole or tetramisole may be used in the treated samples.

According to the art, inhibitors of NAP, such as urea, heat, and/or levamisole exposure of the subsamples should not affect the NAP scores for a patient carrying a Down's syndrome fetus as much as for a patient carrying a normal fetus. Thus, for a Down's syndrome pregnancy, the percentage decrease in NAP score from the untreated, control slide to the exposed or treated slides should be less than for a normal patient. This can be written in terms of the quantities "Delta" as:

$$\Delta_u=[\text{urea exposed NAP score}]/[\text{control NAP score}]$$

and $$\Delta_h=[\text{heat exposed NAP score}]/[\text{control NAP score}].$$

A Down's syndrome pregnancy should have a $\Delta_u$ and $\Delta_h$ greater than a normal pregnancy. By analyzing many cases, the ranges of $\Delta_u$ and $\Delta_h$ can be determined, where the ranges define the high statistical likelihood of Down's syndrome pregnancy as compared with a normal pregnancy.

In the Delta method, the overall phenomenon of urea and heat resistance in Down's syndrome pregnancies is used only after this component of patient-to-patient variation has been removed. The characteristics of this phenomenon are reflected in the statistical determination of what the different ranges of $\Delta_u$ and $\Delta_h$ represent.

A blood smear used to evaluate the presence of alkaline phosphatase in neutrophils can be stained with a solution of naphthol AS-bisphosphate salt and fast red violet LB. AP coverts the soluble colorless substrate to a colored insoluble precipitate. The presence of NAP in the subsample is indicated by the red color of a precipitate formed by enzymatic hydrolysis. Many other AP stains are known to those of skill in the art.

The subsample is usually counter-stained, for example, with hematoxylin, to produce a blue insoluble precipitate in white blood cell nuclei. The stained/counter-stained white blood cells can be identified by having blue nuclei. Neutrophil cells are identified based on the shape and size of the nuclei. Thus, the low magnification processing identifies candidate objects of interest, such as neutrophils, from the color, shape, and size of objects in the image.

Current automated systems have difficulty in evaluating the amount of NAP present on a slide. For NAP, the pathologist usually grades the neutrophils with a rating of 0, 1, 2, 3, or 4 in accordance with a grading scale, such as the one provided with the procedure for using the reagent kit sold by Sigma Diagnostics for demonstrating alkaline phosphatase activity in leukocytes. According to that procedure, a pathologist sums the subjectively assigned ratings for marker identifying precipitate in the first 100 neutrophils to arrive at a score which may be used to determine the relative red intensity of the neutrophils in the cellular sample. This score may then be used to determine whether the condition associated with the presence of the marker is indicated.

The Delta method can also be used to measure acid phosphatase isoenzyme 5 (tartrate-resistant). The demonstration of tartrate-resistant acid phosphatase (TRAP) activity has long been a cornerstone in the diagnosis of hairy cell leukemia (HCL). Acid phosphatase exists as five isoenzymes. While acid phosphatase is present in almost all leukocytes, isoenzyme 5 is restricted to the cells of hairy cell leukemia, as well as some other non-hematopoietic tissues. Isoenzyme 5 is distinguished form other isoenzymes by an inability to be inhibited by tartaric acid. The neoplastic cells in hairy cell leukemia stain strongly positive for acid phosphatase in the presence of tartrate.

The specimen for a TRAP assay can be unstained peripheral blood or bone marrow aspirate smears, anticoagulated peripheral blood or bone marrow, or other body fluids In one method for performing a TRAP assay, subsamples are prepared on slides. Stock solutions are prepared, including (A) pararosanilin-HCl stock (pararosanilin 1 g; distilled water 20 ml; concentrated HCl 5 ml. The pararosanilin is dissolved in the distilled water and hydrochloric acid is added. The resulting solution is heated gently, cooled, filtered, and stored in aliquots in a refrigerator.); (B) sodium nitrite stock (sodium nitrite 2 g; distilled water 50 ml. This solution is prepared fresh or made into 0.4 ml aliquots and stored in a deep freeze.); (c) veronal-acetate buffer stock (sodium acetate ($3H_2O$) 3.88 g; sodium barbitone 5.88 g; distilled water 200 ml); and (D) naphthol ASB1 phosphate stock (naphthol ASB1 phosphate 50 mg; dimethyl formamide 5 ml. This solution is put into 0.5 ml aliquots and stored in a deep freeze.).

Preparation of incubating solution includes the following: First, pararosanilin-HCl (A) 0.4 ml and sodium nitrite (40 mg/ml) (B) 0.4 ml. Pararosanilin is added drop by drop to the thawed sodium nitrite, shaking well after each addition until the solution is corn-colored (leave to stand for at least 30 seconds). Then, naphthol ASB1 phosphate (D) 0.5 ml, veronal acetate buffer stock (c) 2.5 ml, and distilled water 6.5 ml are mixed together well and then added the pararosanilin/sodium nitrite solution. The pH is adjusted to 4.7-5.0, the solution filtered, and used immediately. For demonstrating tartrate resistant acid phosphatase, add 28 mg/10 ml of sodium tartrate to the incubating solution. A control batch without sodium tartrate is used for control sections.

The method of staining is as follows: (1) incubate subsamples for 10-60 sec.; (2) wash well in distilled and then tap water (as the acidity of the solution can make hematoxylin staining muddy); (3) counterstain, with 2% methyl green for 15-30 sec. (hematoxylin can be used as an alternative); (4) wash; and (5) dehydrate, then clear. The results are that acid phosphatase activity stains red.

If at any point the incubating solution is bright red the method must be repeated as this means that the sodium nitrite and pararosanilin have not reacted adequately. The incubating medium should be a slightly opalescent straw color.

The Delta method can also be used to measure α-naphthyl butyrate esterase. α-naphthyl butyrate esterase is a non-specific esterase (NSE) with an activity that is inhibited by fluoride. The presence of α-naphthyl butyrate esterase is a measure of neutrophil functional maturity, since α-naphthyl butyrate esterase is present in higher levels in lymophoblasts than in mature neutrophils. In other words, an increased α-naphthyl butyrate esterase level can indicate leukemia. This cytochemical stain is commonly used for the diagnosis of acute myelogenous leukemias with monocytic differentiation (FAB types M4 and M5) and is part of a routine cytochemical stain panel for the diagnosis of acute leukemia.

In the method of the invention, α-naphthyl butyrate esterase is measured by the Delta method using a non-specific esterase (NSE) assay with α-naphthyl butyrate as a substrate and treatment sodium fluoride. An NSE assay with α-naphthyl butyrate as a substrate no treatment sodium fluoride serves as the control. The specimen can be unstained peripheral blood or bone marrow aspirate smears, anticoagulated peripheral blood or bone marrow, or other body fluids.

In another embodiment, the method measures residual protein immunologically. The method of the invention may use antibodies that are immunoreactive or bind to epitopes of the target proteins. The term "epitope" refers to any antigenic determinant on an antigen to which the paratope of an antibody binds. Epitopes usually consist of chemically active surface groupings of molecules such as amino acids or sugar side chains and usually have specific three dimensional structural characteristics, as well as specific charge characteristics. The term "antibody" includes intact molecules as well as fragments thereof, such as Fab, Fab', F(ab')$_2$, Fv, and single chain antibody that can bind the epitope. These antibody fragments retain some ability to bind selectively with antigen or receptor. The antibody may consist essentially of pooled monoclonal antibodies with different epitopic specificities, as well as distinct monoclonal antibody preparations. Monoclonal antibodies are made from antigen containing fragments of the protein by methods well known in the art (see, Kohler, et al., *Nature* 256: 495, 1975; *Current Protocols in Molecular Biology*, Ausubel et al., ed., 1989). Methods of making these fragments are known in the art (see, for example, Harlow & Lane, *Antibodies: A Laboratory Manual*, Cold Spring Harbor Laboratory, New York, 1997). If needed, polyclonal or monoclonal antibodies can be further purified, for example, by binding to and elution from a matrix to which the peptide or a peptide to which the antibodies are raised is bound. Those of skill in the art will know of various techniques common in the immunology arts for purification and/or concentration of polyclonal antibodies, as well as monoclonal antibodies (see, e.g., Colligan et al., Unit 9, *Current Protocols in Immunology*, Wiley Interscience, 1997). Antibodies, including polyclonal and monoclonal antibodies, chimeric antibodies, single chain antibodies and the like, have with the ability to bind with high immunospecificity to the target proteins. Antibodies may be employed in known immunological procedures for qualitative or quantitative detection of these proteins in cells, tissue samples, sample preparations or fluids. These antibodies can be unlabeled or suitably labeled with chromogenic dyes, fluorogenic dyes, or coupled to enzymes that catalyze chromogenic or fluorogenic reactions. Thus, the binding of antibody to target protein is assayable by image analysis.

ELISA or other immunoaffinity methods can be used to quantify protein. ELISA refers to an enzyme-linked immunosorbant assay method for detecting antigens or antibodies using enzyme-substrate reactions. The enzymes are generally coupled to antibodies (either to antibodies specific for the antigen or to anti-immunoglobulin). The amount of enzyme conjugate determined from the turnover of an appropriate substrate, preferably one that produces a colored product.

The Delta Method may be further performed with an automated system. Such an automated system will quantify the various samples and subsamples and calculate a Delta. The automated method will be further understood with reference to the description below.

Automated System

The invention provides a method for automated cell image analysis that eliminates the need for operator input to locate cell objects for analysis.

A slide prepared with a subsample and reagent is placed in a slide carrier which preferably holds four slides. The slide carriers are loaded into an input hopper. The operator enters data identifying the size, shape and location of a scan area on each slide, or, preferably, the system automatically locates a scan area for each slide during slide processing. The operator then activates the system for slide processing. At system activation, a slide carrier is positioned on an X-Y stage of an optical system. Any bar codes used to identify slides are then read and stored for each slide in a carrier. The entire slide is rapidly scanned at a low magnification, typically 10×. At each location of the scan, a low magnification image is acquired and processed to detect candidate objects of interest. Preferably, color, size and shape are used to identify objects of interest. The location of each candidate object of interest is stored.

At the completion of the low level scan for each slide in the carrier on the stage, the optical system is adjusted to a high magnification such as 40× or 60×, and the X-Y stage is positioned to the stored locations for the candidate objects of interest on each slide in the carrier. A high magnification image is acquired for each candidate object of interest and a series of image processing steps are performed to confirm the analysis which was performed at low magnification. A high magnification image is stored for each continued object or interest. These images are then available for retrieval by a pathologist or cytotechnologist to review for final diagnostic evaluation. Having stored the location of each object of interest, a mosaic comprised of the candidate objects of interest for a slide may be generated and stored. The pathologist or cytotechnologist may view the mosaic or may also directly view the slide at the location of an object of interest in the mosaic for further evaluation. The mosaic may be stored on magnetic media for future reference or may be transmitted to a remote site for review or storage. The entire process involved in examining a single slide takes on the order of 9-15 minutes (min) depending on scan area size and the number of detected candidate objects of interest.

The processing of images acquired in the automated scanning of the present invention preferably includes the steps of transforming the image to a different color space; filtering the transformed image with a low pass filter; dynamically thresholding the pixels of the filtered image to suppress background material; performing a morphological function to remove artifacts from the thresholded image; analyzing the thresholded image to determine the presence of one or more regions of connected pixels having the same color; and categorizing every region having a size greater than a minimum size as a candidate object of interest.

In another aspect of the invention, the scan area is automatically determined by scanning the slide; acquiring an image at each slide position; analyzing texture information or each image to detect the edges of the subsample; and storing the locations corresponding to the detected edges to define the scan area.

According to yet another aspect of the invention, automated focusing of the optical system is achieved by initially determining a focal plane from an array of points or locations in the scan area. The derived focal plane enables subsequent rapid automatic focusing in the low power scanning operation. The focal plane is determined by determining proper focal positions across an array of locations and performing an analysis such as a least squares fit of the array of focal positions to yield a focal plane across the array. Preferably, a focal position at each location is determined by incrementing the position of a Z stage for a fixed number of coarse and fine iterations. At each iteration, an image is acquired and a pixel variance or other optical parameter about a pixel mean for the acquired image is calculated to form a set of variance data. A least squares fit is performed on the variance data according to a known function. The peak value of the least squares fit curve is selected as an estimate of the best focal position.

In another aspect of the present invention, another focal position method for high magnification locates a region of interest centered about a candidate object of interest within a slide which were located during an analysis of the low magnification images. The region of interest is preferably n columns wide, where n is a power of 2. The pixels of this region are then processed using a Fast Fourier Transform to generate a spectra of component frequencies and corresponding complex magnitude for each frequency component. Preferably, the complex magnitude of the frequency components which range from 25% to 75% of the maximum frequency component are squared and summed to obtain the total power for the region of interest. This process is repeated for other Z positions and the Z position corresponding to the maximum total power for the region of interest is selected as the best focal position. This process is preferably used to select a Z position for regions of interest for slides containing neutrophils stained with Fast Red to identify alkaline phosphataase in cell cytoplasm and counter-stained with hematoxylin to identify the nucleus of the neutrophil cell. This focal method may be used with other stains and types of cellular specimens.

In still another aspect of the invention, a method for automated slide handling is provided. A slide is mounted onto a slide carrier with a number of other slides side-by-side. The slide carrier is positioned in an input feeder with other slide carriers to facilitate automatic analysis of a batch of slides. The slide carrier is loaded onto the X-Y stage of the optical system for the analysis of the slides thereon. Subsequently, the first slide carrier is unloaded into an output feeder after automatic image analysis and the next carrier is automatically loaded.

Figure 2:
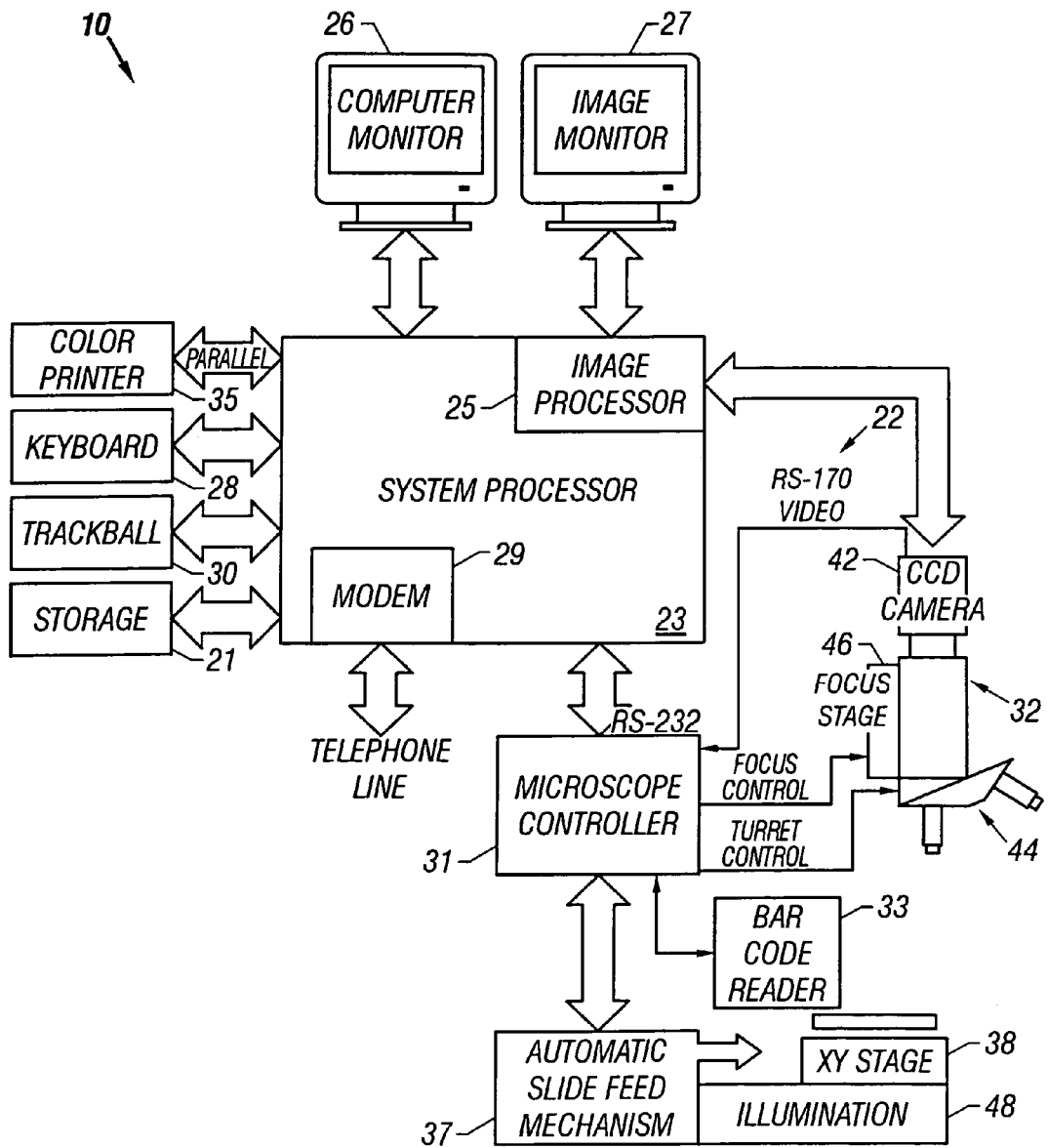
FIG. 2 is a block diagram of the apparatus shown in FIG. 1.

Referring to the FIGURES, an apparatus for automated cell image analysis of cellular specimens is generally indicated by reference numeral 10 as shown in perspective view in FIG. 1 and in block diagram form in FIG. 2. The apparatus 10 comprises a microscope subsystem 32 housed in a housing 12. The housing 12 includes a slide carrier input hopper 16 and a slide carrier output hopper 18. A door 14 in the housing 12 secures the microscope subsystem from the external environment. A computer subsystem comprises a computer 22 having a system processor 23, an image processor 25 and a communications modem 29. The computer subsystem further includes a computer monitor 26 and an image monitor 27 and other external peripherals including storage device 21, track ball device 30, keyboard 28 and color printer 35. An external power supply 24 is also shown for powering the system. Viewing oculars 20 of the microscope subsystem project from the housing 12 for operator viewing. The apparatus 10 further includes a CCD camera 42 for acquiring images through the microscope subsystem 32. A microscope controller 31 under the control of system processor 23 controls a number of microscope subsystem functions described further in detail. An automatic slide feed mechanism 37 in conjunction with X-Y stage 38 provide automatic slide handling in the apparatus 10. An illumination light source 48 projects light onto the X-Y stage 38 which is subsequently imaged through the microscope subsystem 32 and acquired through CCD camera 42 for processing in the image processor 25. A Z stage or focus stage 46 under control of the microscope controller 31 provides displacement of the microscope subsystem in the Z plane for focusing. The microscope subsystem 32 further includes a motorized objective turret 44 for selection of objectives.

The purpose of the apparatus 10 is for the unattended automatic scanning of prepared microscope slides for the detection and counting of candidate objects of interest such as cells. The preferred embodiment may be utilized for rare event detection in which there may be only one candidate object of interest per several hundred thousand normal cells, e.g., one to five candidate objects of interest per 2 square centimeter area of the slide. The apparatus 10 automatically locates and counts candidate objects of interest and estimates normal cells present in a cellular specimen on the basis of color, size and shape characteristics. A number of stains are used to preferentially stain candidate objects of interest and normal cells different colors, so that such cells can be distinguished from each other. A subsample can be prepared with a reagent to obtain a colored insoluble precipitate. The apparatus is used to detect this precipitate as a candidate object of interest.

Figure 8:
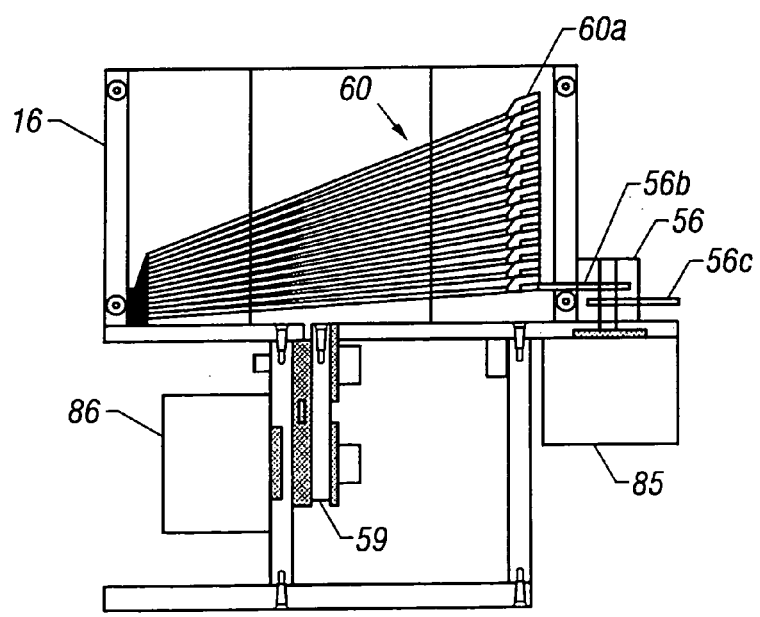
FIG. 8 shows end views of the input module of the automated slide handling subsystem.
Figure 8A:
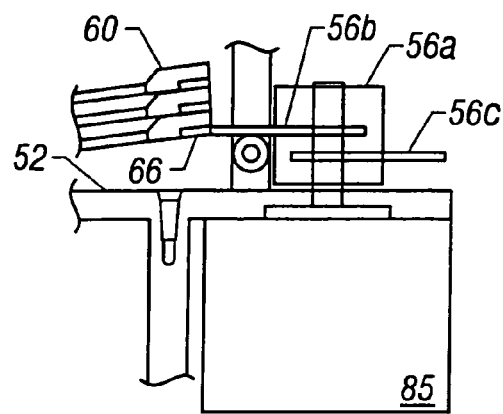
FIGS. 8a-8d illustrate the input operation of the automatic slide handling subsystem.
Figure 8B:
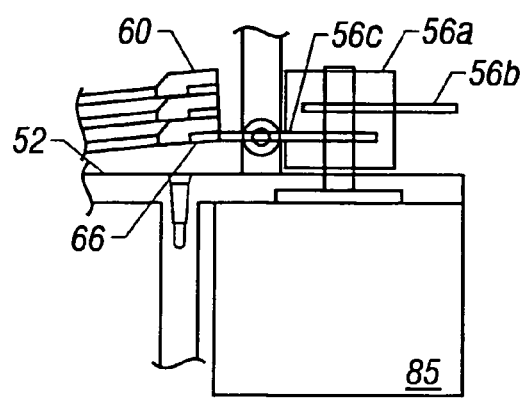

During operation of the apparatus 10, a pathologist or laboratory technician mounts prepared slides onto slide carriers. A slide carrier 60 is illustrated in FIG. 8 and are described further below. Each slide carrier holds up to 4 slides. Up to 25 slide carriers are then loaded into input hopper 16. The operator can specify the size, shape and location of the area to be scanned or alternatively, the system can automatically locate this area. The operator then commands the system to begin automated scanning of the slides through a graphical user interface. Unattended scanning begins with the automatic loading of the first carrier and slide onto the precision motorized X-Y stage 38. A bar code label affixed to the slide is read by a bar code reader 33 during this loading operation. Each slide is then scanned at a user selected low microscope magnification, for example, 10×, to identify candidate cells based on their color, size and shape characteristics. The X-Y locations of candidate cells are stored until scanning is completed.

After the low magnification scanning is completed, the apparatus automatically returns to each candidate cell, reimages and refocuses at a higher magnification such as 40× and performs further analysis to confirm the cell candidate. The apparatus stores an image of the cell for later review by a pathologist. All results and images can be stored to a storage device 21 such as a removable hard drive or DAT tape or transmitted to a remote site for review or storage. The stored images for each slide can be viewed in a mosaic of images for further review. In addition, the pathologist or operator can also directly view a detected cell through the microscope using the included oculars 20 or on image monitor 27.

Figure 3:
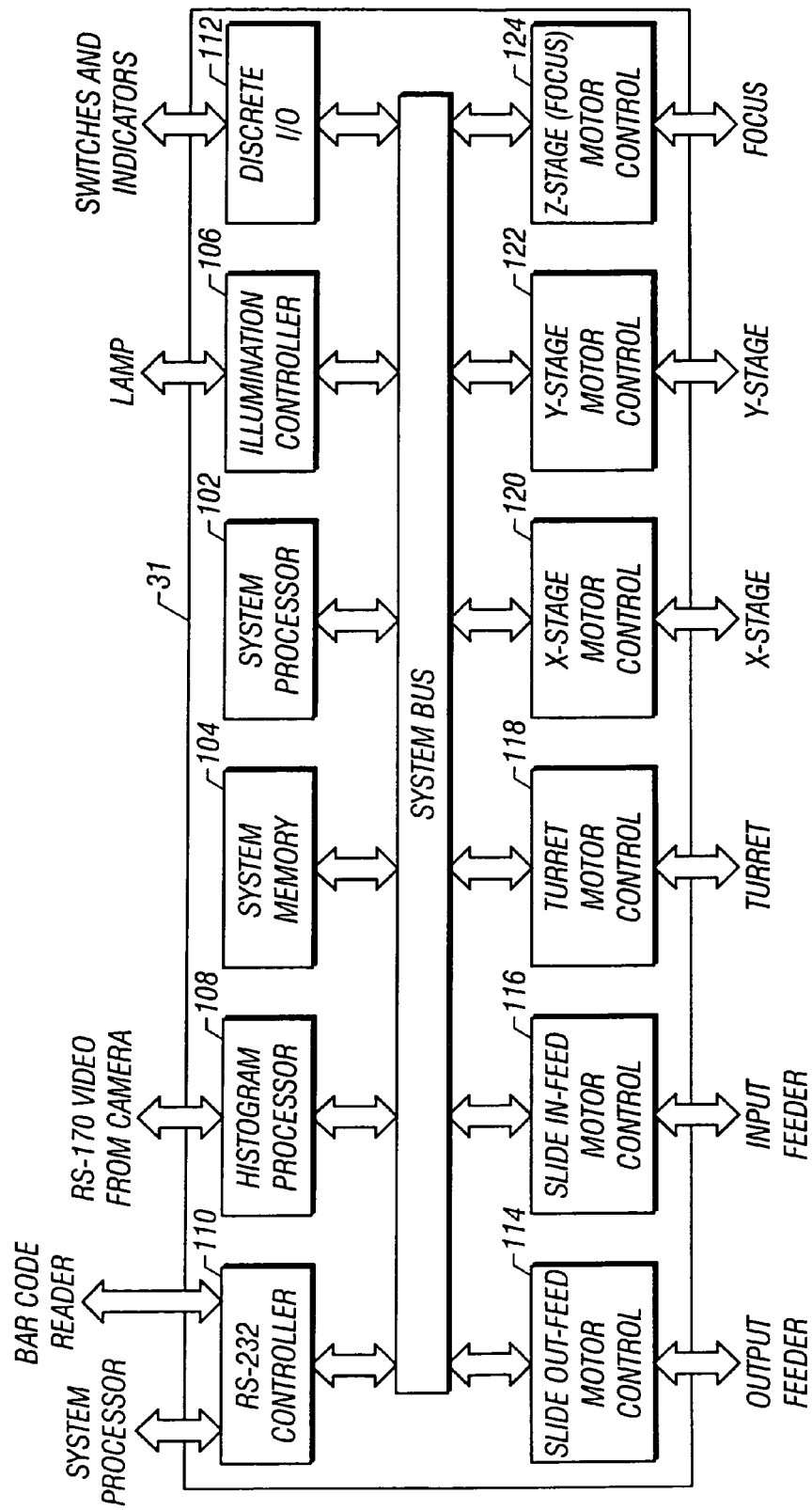
FIG. 3 is a block diagram of the microscope controller of FIG. 2.

Having described the overall operation of the apparatus 10 from a high level, the further details of the apparatus are now be described. Referring to FIG. 3, the microscope controller 31 is shown in more detail. The microscope controller 31 includes a number of subsystems connected through a system bus. A system processor 102 controls these subsystems and is controlled by the apparatus system processor 23 through an RS 232 controller 110. The system processor 102 controls a set of motor-control subsystems 114 through 124 which control the input and output feeder, the motorized turret 44, the X-Y stage 38, and the Z stage 46 (FIG. 9). The histogram processor 108 receives input from CCD camera 42 for computing variance data during the focusing operation described further herein.

The system processor 102 further controls an illumination controller 106 for control of substage illumination 48. The light output from the halogen light bulb which supplies illumination for the system can vary over time due to bulb aging, changes in optical alignment, and other factors. In addition, slides which have been "over stained" can reduce the camera exposure to an unacceptable level. To compensate for these effects, the illumination controller 106 is included. This controller is used in conjunction with light control software to compensate for the variations in light level. The light control software samples the output from the camera at intervals (such as between loading of slide carriers), and commands the controller to adjust the light level to the desired levels. In this way, light control is automatic and transparent to the user and adds no additional time to system operation.

The system processor 23 is preferably an IBM compatible PC with an Intel Pentium 90 MHZ processor, 32 MB of RAM, and two IGB hard drives with one hard drive being removable. The operating system for system processor 23 is Windows for Workgroups 3.1 available from Microsoft Corporation (Redmond, Wash.). Image processor 25 is preferably a Matrox Imaging Series 640 board set available from Matrox Electronics Systems, Ltd. (Dorval, Quebec, Calif.). The preferred image processor is provided with support software and the Matrox Imaging Library (MIL). Microscope controller system processor 102 is an Advanced Micro Devices AMD29K device.

Figure 4:
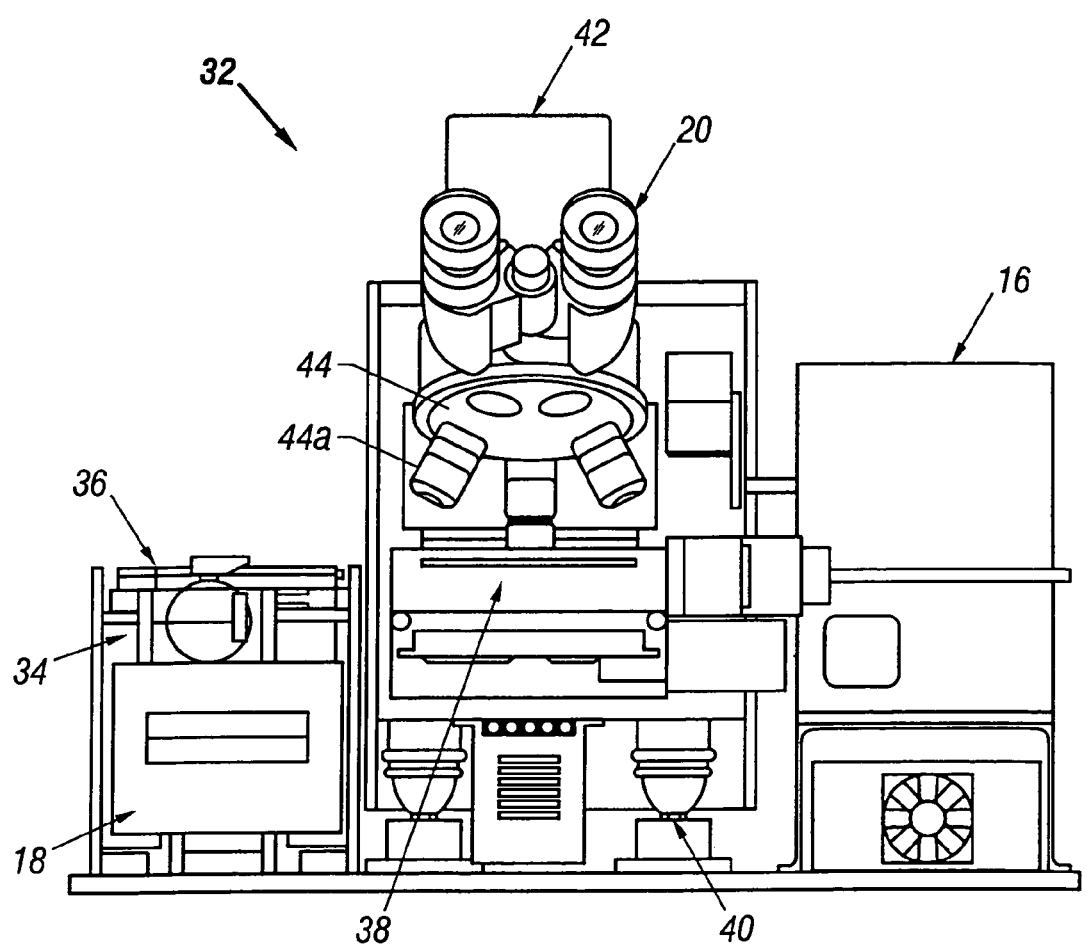
FIG. 4 is a plan view of the apparatus of FIG. 1 having the housing removed.
Figure 5:
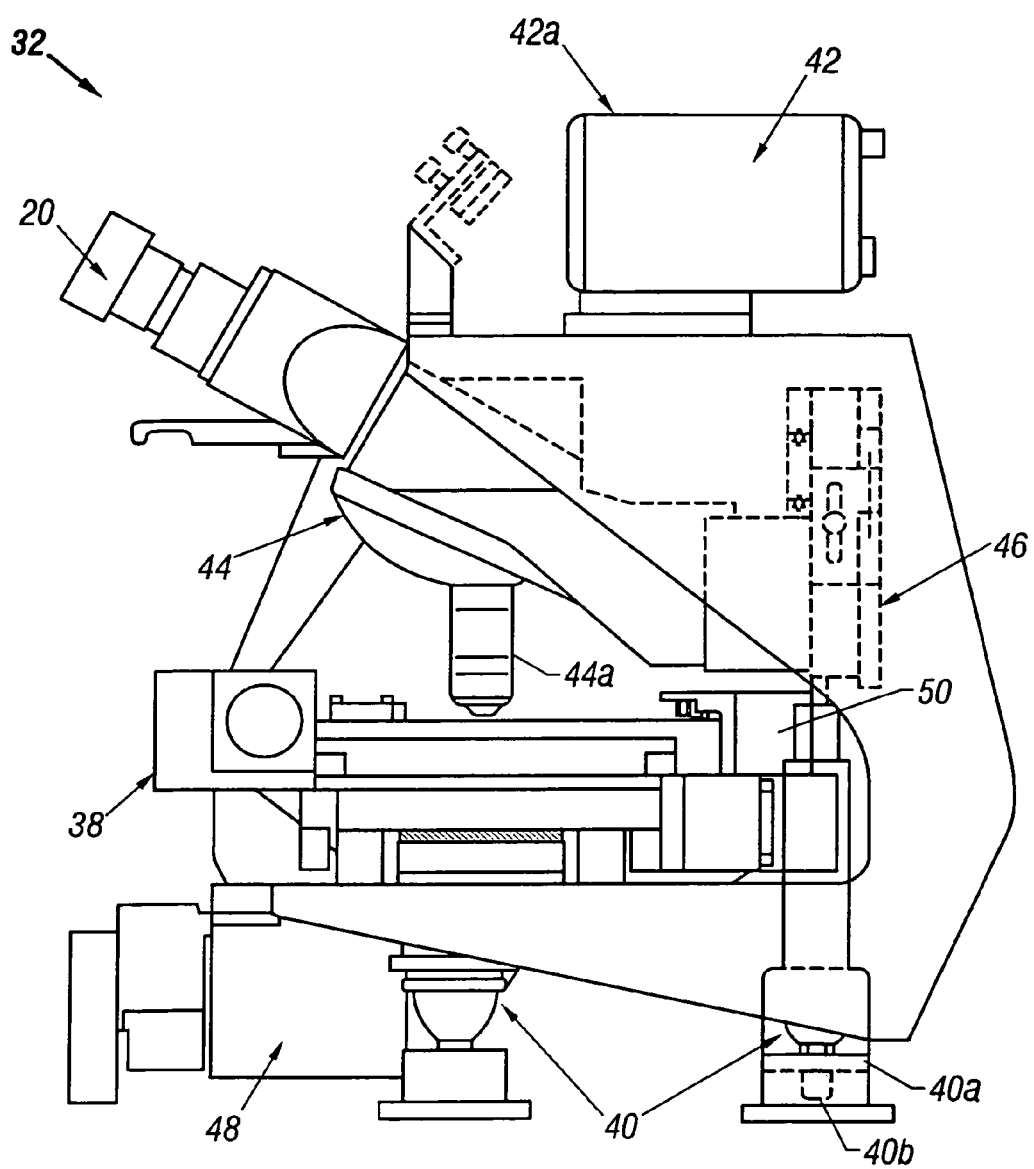
FIG. 5 is a side view of a microscope subsystem of the apparatus of FIG. 1.

Referring now to FIGS. 4 & 5, further detail of the apparatus 10 is shown. FIG. 4 shows a plan view of the apparatus 10 with the housing 12 removed. A portion of the automatic slide feed mechanism 37 is shown to the left of the microscope subsystem 32 and includes slide carrier unloading assembly 34 and unloading platform 36 which in conjunction with slide carrier unloading hopper 18 function to receive slide carriers which have been analyzed.

Vibration isolation mounts 40, shown in further detail in FIG. 5, are provided to isolate the microscope subsystem 32 from mechanical shock and vibration that can occur in a Apical laboratory environment. In addition to external sources of vibration, the high speed operation of the X-Y stage 38 can induce vibration into the microscope subsystem 2. Such sources of vibration can be isolated from the electro-optical subsystems to avoid any undesirable effects on image quality. The isolation mounts 40 comprise a spring 40a and piston 40b submerged in a high viscosity silicon gel which is enclosed in an elastomer membrane bonded to a casing to achieve damping factors on the order of 17% to 20%.

Figure 6A:
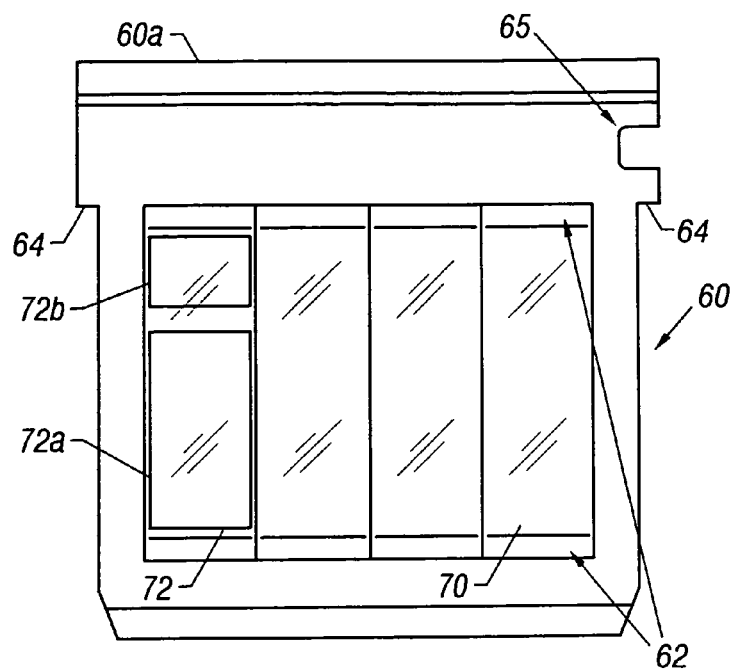
FIG. 6a is a top view of a slide carrier for use levity the apparatus of FIG. 1.
Figure 6B:
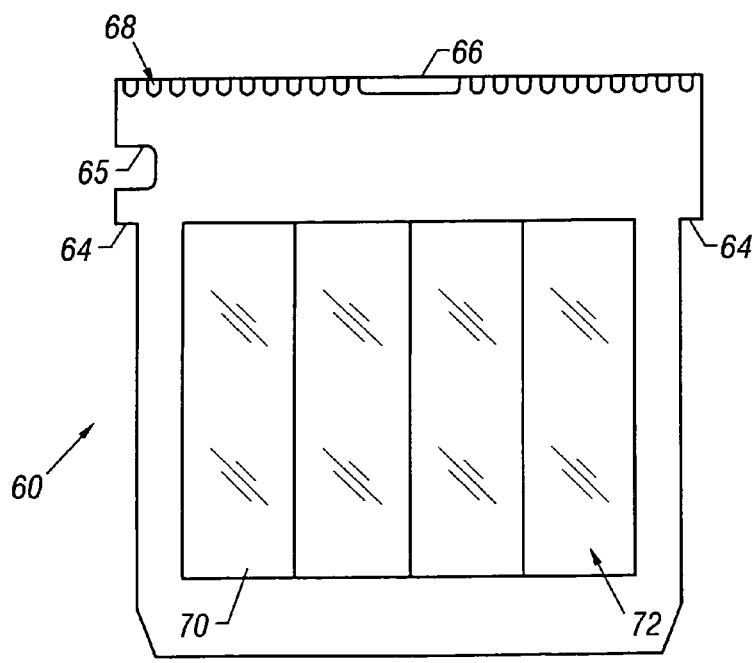

The automatic slide handling feature of the present invention is now described. The automated slide handling subsystem operates on a single slide carrier at a time. A slide carrier 60 is shown in FIG. 6a & 6b which provide a top view and a bottom view, respectively. The slide carrier 60 includes up to four slides 70 mounted with adhesive tape 62. The carrier 60 includes ears 64 for hanging the carrier in the output hopper 18. An undercut 66 and pitch rack 68 are formed at the top edge of the slide carrier 60 for mechanical handling of the slide carrier. A keyway cutout 65 is formed in one side of the carrier 60 to facilitate carrier alignment. A prepared slide 72 mounted on the slide carrier 60 includes a sample area 72a and a bar code label area 72b.

Figure 7A:
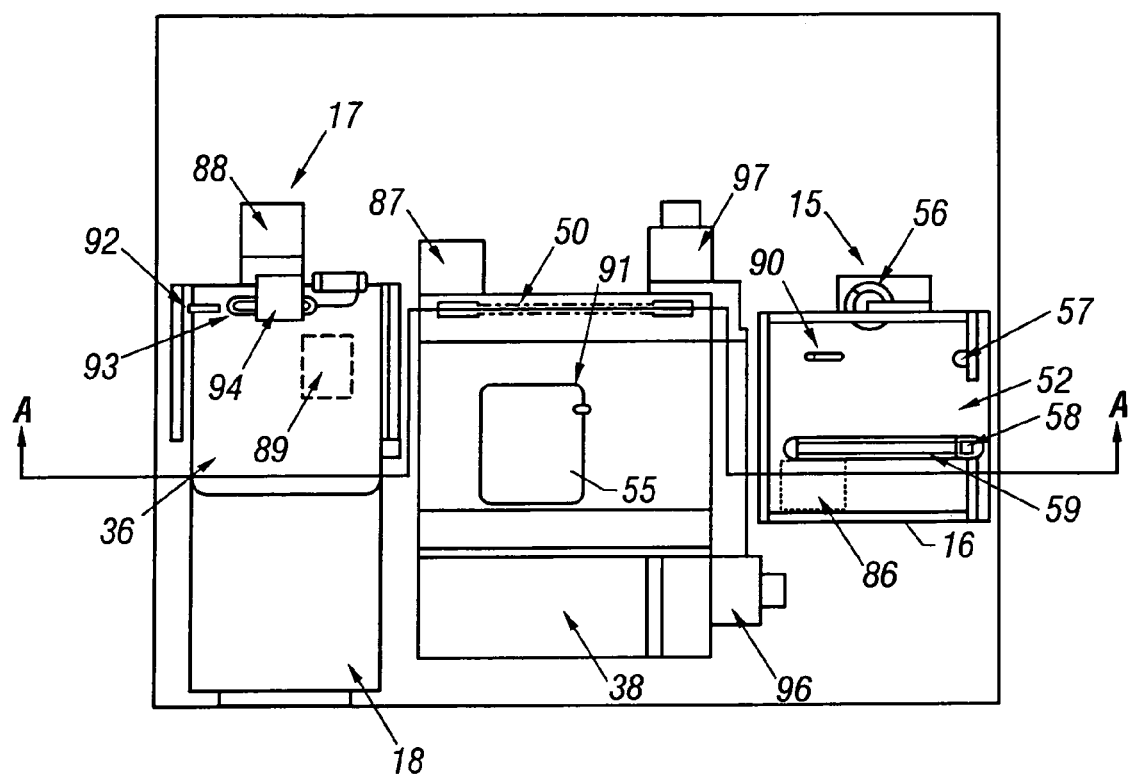
FIG. 7a is a top view of an automated slide handling subsystem of the apparatus of FIG. 1.
Figure 7B:
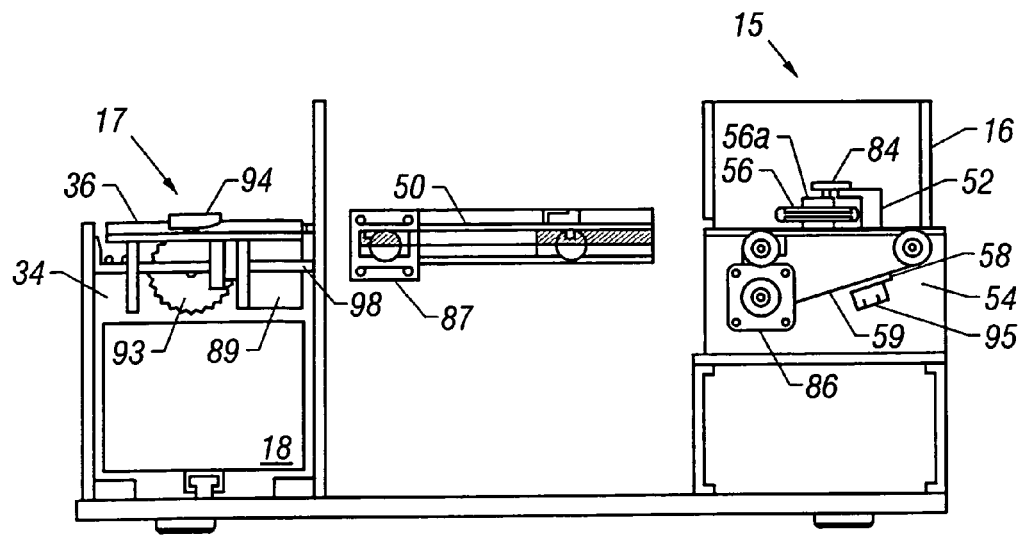
FIG. 7b is a partial cross-sectional view of the automated slide handling subsystem of FIG. 7a taken on line A-A.

FIG. 7a provides a top view of the slide handling subsystem which comprises a slide input module 15, a slide output module 17 and X-Y stage drive belt 50. FIG. 7b provides a partial cross-sectional view taken along line A-A of FIG. 7a.

The slide input module 15 includes a slide carrier input hopper 16, loading platform 52 and slide carrier loading subassembly 54. The input hopper 16 receives a series of slide carriers 60 (FIG. 6a & 6b) in a stack on loading platform 52. A guide key 57 protrudes from a side of the input hopper 16 to which the keyway cutout 65 (FIG. 6a) of the carrier is fit to achieve proper alignment.

The input module 15 further includes a revolving indexing cam 56 and a switch 90 mounted in the loading platform 52, the operation of which is described further below. The carrier subassembly 54 comprises an infeed drive belt 59 driven by a motor 86. The infeed drive belt 59 includes a pusher tab 58 for pushing the slide carrier horizontally toward the X-Y stage 38 when the belt is driven. A homing switch 95 senses the pusher tab 58 during a revolution of the belt 59.

Referring specifically to FIG. 7a, the X-Y stage 38 is shown with x position and y postion motors 96 and 97 respectively which are controlled by the microscope controller 31 (FIG. 3) and are not considered part of the slide handling subsystem. The X-Y stage 38 further includes an aperture 55 for allowing illumination to reach the slide carrier. A switch 91 is mounted adjacent the aperture 55 for sensing contact with the carrier and thereupon activating a motor 87 to drive stage drive belt 50 (FIG. 7b). The drive belt 50 is a double sided timing belt having teeth for engaging pitch rack 68 of the carrier 60 (FIG. 6b).

The slide output module 17 includes slide carrier output hopper 18, unloading platform 6, and slide carrier unloading subassembly 34. The unloading subassembly 34 comprises a motor 89 for rotating the unloading platform 36 about shaft 98 during an unloading operation described further below. An outfeed gear 93 driven by motor 88 rotatably engages the pitch rack 68 of the carrier 60 (FIG. 6b) to transport the carrier to a rest position against switch 92. A springloaded hold-down mechanism holds the carrier in place on the unloading platform 36.

The slide handling operation is now described. Referring to FIG. 8, a series of slide carriers 60 are shown stacked in input hopper 16 with the top edges 60a aligned. As the slide handling operation begins, the indexing cam 56 driven by motor 85 advances one revolution to allow only one slide carrier to drop to the bottom of the hopper 16 and onto the loading platform 52.

Figure 8C:
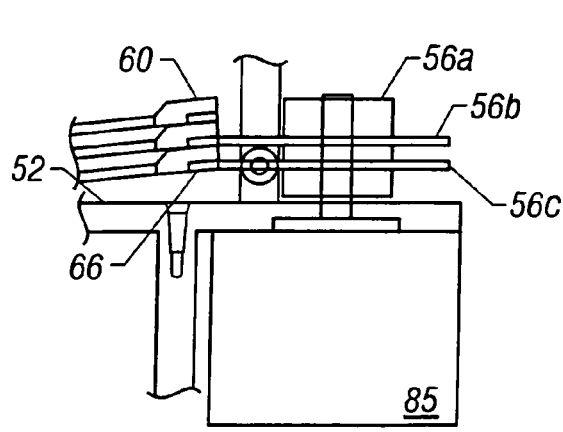
Figure 8D:
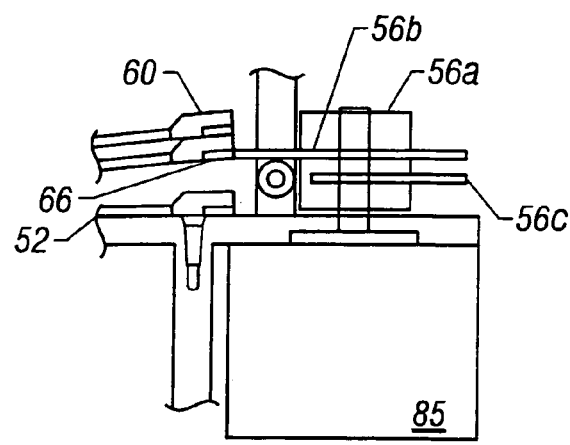

FIGS. 8a-8d show the cam action in more detail. The indexing cam 56 includes a hub 56a to which are mounted upper and lower leaves 56b and 56c respectively. The leaves 56b, 56c are semicircular projections oppositely positioned and spaced apart vertically. In a first position shown in FIG. 8a, the upper leaf 56b supports the bottom carrier at the undercut portion 66. At a position of the indexing cam 56 rotated 180°, shown in FIG. 8b, the upper leaf 56b no longer supports the carrier and instead the carrier has dropped slightly and is supported by the lower leaf 56c. FIG. 8c shows the position of the cam 56 rotated 270° wherein the upper leaf 56b has rotated sufficiently to begin to engage the undercut 66 of the next slide carrier while the opposite facing lower leaf 56c still supports the bottom carrier. After a full rotation of 360° as shown in FIG. 8d, the lower leaf 56c has rotated opposite the carrier stack and no longer supports the bottom carrier which now rests on the loading platform 52. At the same position, the upper leaf 56b supports the next carrier for repeating the cycle.

Referring again to FIG. 7a & 7b, when the carrier drops to the loading platform 52, the contact closes switch 90 which activates motors 86 and 87. Motor 86 drives the infeed drive belt 59 until the pusher tab 58 makes contact with the carrier and pushes the carrier onto the X-Y stage drive belt 50. The stage drive belt 50 advances the carrier until contact is made with switch 91, the closing of which begins the slide scanning process described further herein. Upon completion of the scanning process, the X-Y stage 38 moves to an unload position and motors 8, and 88 are activated to transport the carrier to the unloading platform 36 using stage drive belt 50. Motor 88 drives outfeed gear 93 to engage the carrier pitch rack 68 of the carrier 60 (FIG. 6b) until switch 92 is contacted. Closing switch 92 activates motor 89 to rotate the unloading platform 36.

The unloading operation is shown in more detail in end views of the output module 17 (FIGS. 9a-9d). In FIG. 9a, the unloading platform 36 is shown in a horizontal position supporting a slide carrier 60. The hold-down mechanism 94 secures the carrier 60 at one end. FIG. 9b shows the output module 17 after motor 89 has rotated the unloading platform 36 to a vertical position, at which point the spring loaded hold-down mechanism 94 releases the slide carrier 60 into the output hopper 18. The carrier 60 is supported in the output hopper 18 by means of ears 64 (FIG. 6a & 6b). FIG. 9c shows the unloading platform 16 being rotated back towards the horizontal position. As the platform 36 rotates upward, it contacts the deposited carrier 60 and the upward movement pushes the carrier toward the front of the output hopper 18. FIG. 9d shows the unloading platform 36 at the original horizontal position after having output a series of slide carriers 60 to the output hopper 18.

Having described the overall system and the automated slide handling feature, the aspects of the apparatus 10 relating to scanning, focusing and image processing is now described in further detail.

In some cases, an operator knows where the scan area of interest is on the slide. Conventional preparation of slides for examination provides repeatable and known placement of the sample on the slide. The operator can therefore instruct the system to always scan the same area at the same location of every slide which is prepared in this fashion. At other times, the area of interest is not known, for example, where slides are prepared manually with a known smear technique. One feature of the invention automatically determines the scan area using a texture analysis process.

Figure 10:
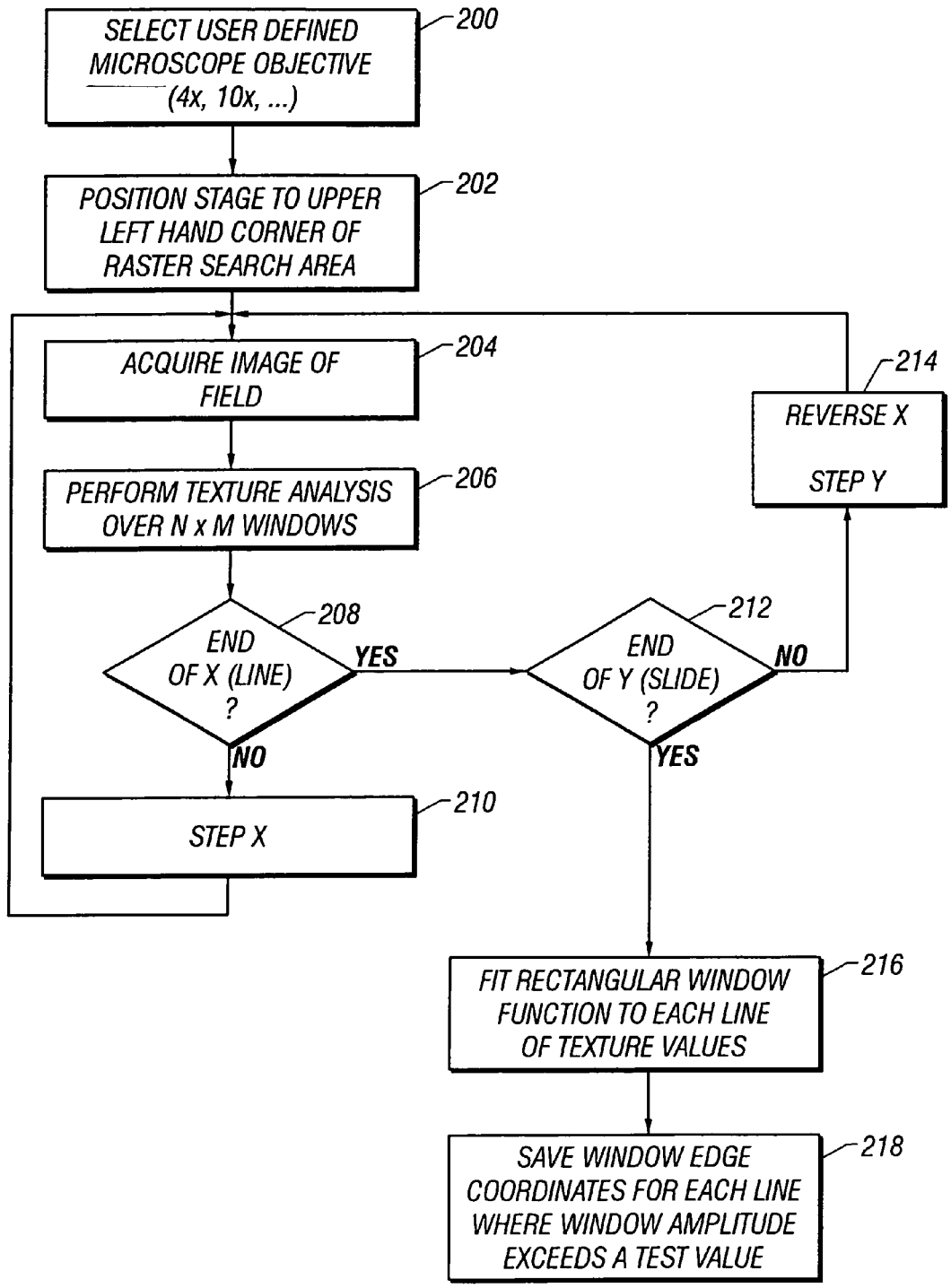
FIG. 10 is a flow diagram of the procedure for automatically determining a scan area.

FIG. 10 is a flow diagram that describes the processing associated with the automatic location of a scan area. As shown in FIG. 10, the basic method is to pre-scan the entire slide area to determine texture features that indicate the presence of a smear and to discriminate these areas from dirt and other artifacts.

Figure 12:
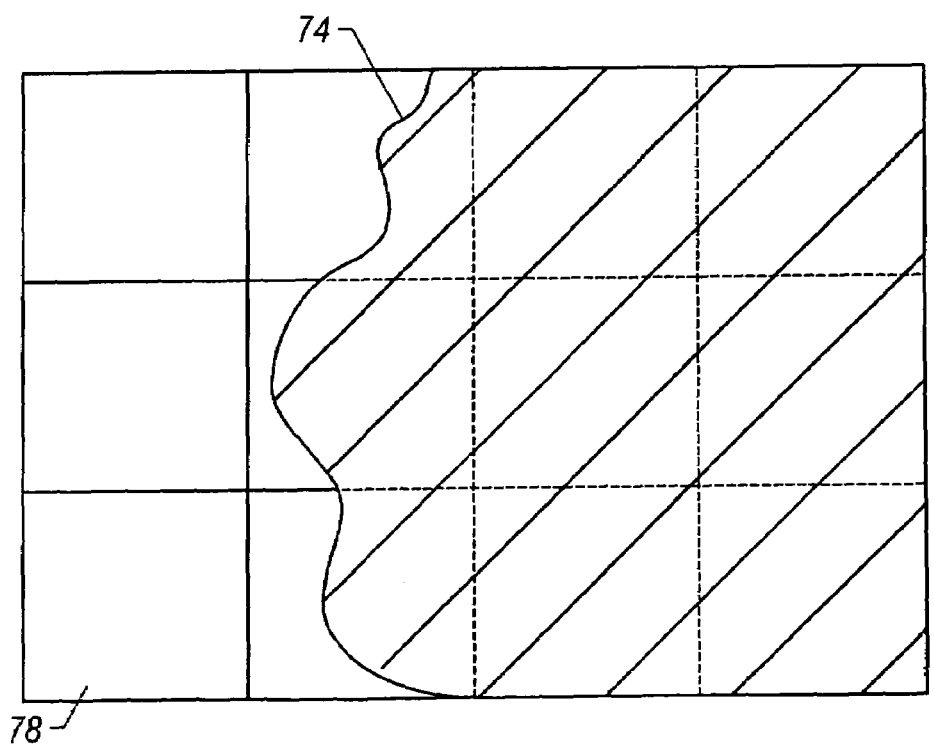
FIG. 12 illustrates an image of a field acquired in the procedure of FIG. 10.

At each location of this scan, an image such as in FIG. 12 is acquired and analyzed for texture information at steps 204 and 206. Since it is desired to locate the edges of the smear sample within a given image, texture analyses are conducted over areas called windows 78, which are smaller than the entire image as shown in FIG. 12. The process iterates the scan across the slide at steps 208, 210, 212, and 214.

Figure 11:
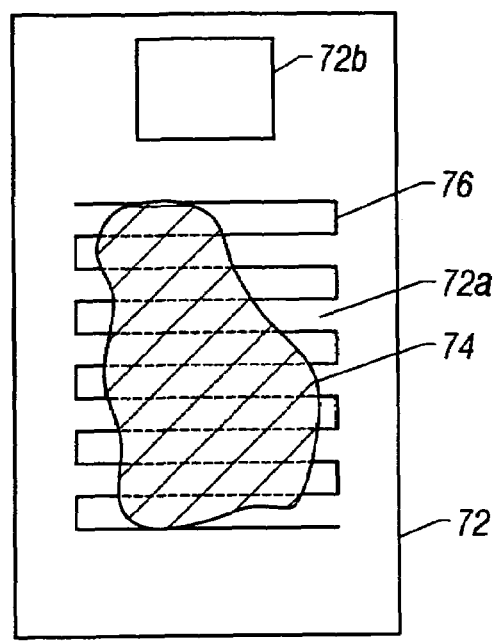
FIG. 11 shows the scan path on a prepared slide in the procedure of FIG. 10.

In the interest of speed, the texture analysis process is performed at a lower magnification, preferably at a 4× objective. One reason to operate at low magnification is to image the largest slide area at any one time. Since cells do not yet need to be resolved at this stage of the overall image analysis, the 4× magnification is preferred. On a typical slide, as shown in FIG. 11, a portion 72*b* of the end of the slide 72 is reserved for labeling with identification information. Excepting this label area, the entire slide is scanned in a scan fashion 76 to yield a number of adjacent images.

Texture values for each window include the pixel variance over a window, the difference between the largest and smallest pixel value within a window, and other indicators. The presence of a smear raises the texture values compared with a blank area.

One problem with a smear is the non-uniform thickness and texture. For example, the smear is likely to be relatively thin at the edges and thicker towards the middle due to the nature of the smearing process. To accommodate for the non-uniformity, texture analysis provides a texture value for each analyzed area. The texture tends to gradually rise as the scan proceeds across a smear from a thin area to a thick area, reaches a peak, and then falls off again to a lower value as a thin area at the edge is reached. The problem is then to decide from the series of texture values the beginning and ending, or the edges, of the smear. The texture values are fit to a square wave waveform since the texture data does not have sharp beginnings and endings.

After conducting this scanning and texture evaluation operation, one must determine which areas of elevated texture values represent the desired smear 74, and which represent undesired artifacts. This determination is accomplished by fitting a step function, on a line by line basis to the texture values in step 216. This function, which resembles a single square wave across the smear with a beginning at one edge, and end at the other edge, and an amplitude provides the means for discrimination. The amplitude of the best-fit step function is utilized to determine whether smear or dirt is present since relatively high values indicate smear. If a smear is present, the beginning and ending coordinates of this pattern are noted until all lines have been processed, and the smear sample area defined at 218.

After an initial focusing operation described further herein, the scan area of interest is scanned to acquire images for image analysis. The preferred method of operation is to initially perform a complete scan of the slide at low magnification to identify and locate candidate objects of interest, followed by further image analysis of the candidate objects of interest at high magnification to confirm the objects as cells. An alternate method of operation is to perform high magnification image analysis of each candidate object of interest; immediately after the object has been identified at low magnification. The low magnification scanning then resumes, searching for additional candidate objects of interest. Since it takes on the order of a few seconds to change objectives, this alternate method of operation would take longer to complete.

The operator can pre-select a magnification level to be used for the scanning operation. A low magnification using a 10× objective is preferred for the scanning operation since a larger area can be initially analyzed for each acquired scan image. The overall detection process for a cell includes a combination of decisions made at both low (10×) and high magnification (40×) levels. Decision making at the 10× magnification level is broader in scope, i.e., objects that loosely fit the relevant color, size and shape characteristics are identified at the 10× level. Analysis at the 40× magnification level then proceeds to refine the decision making and confirm objects as likely cells or candidate objects of interest. For example, at the 40× level, some objects that were identified at 10× are artifacts which the analysis process then rejects. In addition, closely packed objects of interest appearing at 10× are separated at the 40× level.

When a cell straddles or overlaps adjacent image fields, image analysis of the individual adjacent image fields could result in the cell being rejected or undetected. To avoid missing such cells, the scanning operation compensates by overlapping adjacent image fields in both the x and y directions. An overlap amount greater than half the diameter of an average cell is preferred. In the preferred embodiment, the overlap is specified as a percentage of the image field in the x and y directions.

The time to complete an image analysis can vary depending upon the size of the scan area and the number of candidate cells, or objects of interest identified. For one example, in the preferred embodiment, a complete image analysis of a scan area of two square centimeters in which 50 objects of interest are confirmed can be performed in about 12 to 15 min. This example includes not only focusing, scanning and image analysis but also the saving of 40× images as a mosaic on hard drive 21 (FIG. 2).

How ever the scan area is defined, an initial focusing operation must be performed on each slide prior to scanning. This focusing operation is required, since slides differ, in general, in their placement in a carrier. These differences include slight (but significant) variations of tilt of the slide in the carrier. Since each slide must remain in focus during scanning, the degree of tilt of each slide must be determined. This determination is accomplished with an initial focusing operation that determines the exact degree of tilt, so that focus can be maintained automatically during scanning.

The initial focusing operation and other focusing operations to be described later utilize a focusing method based on processing of images acquired by the system. This method was chosen for simplicity over other methods including use of beams reflected from the slide surface and use of mechanical gauges. These other methods also would not function properly when the subsample is protected with a cover glass. The preferred method results in lower system cost and improved reliability, since no additional parts need be included to perform focusing.

Figure 13A:
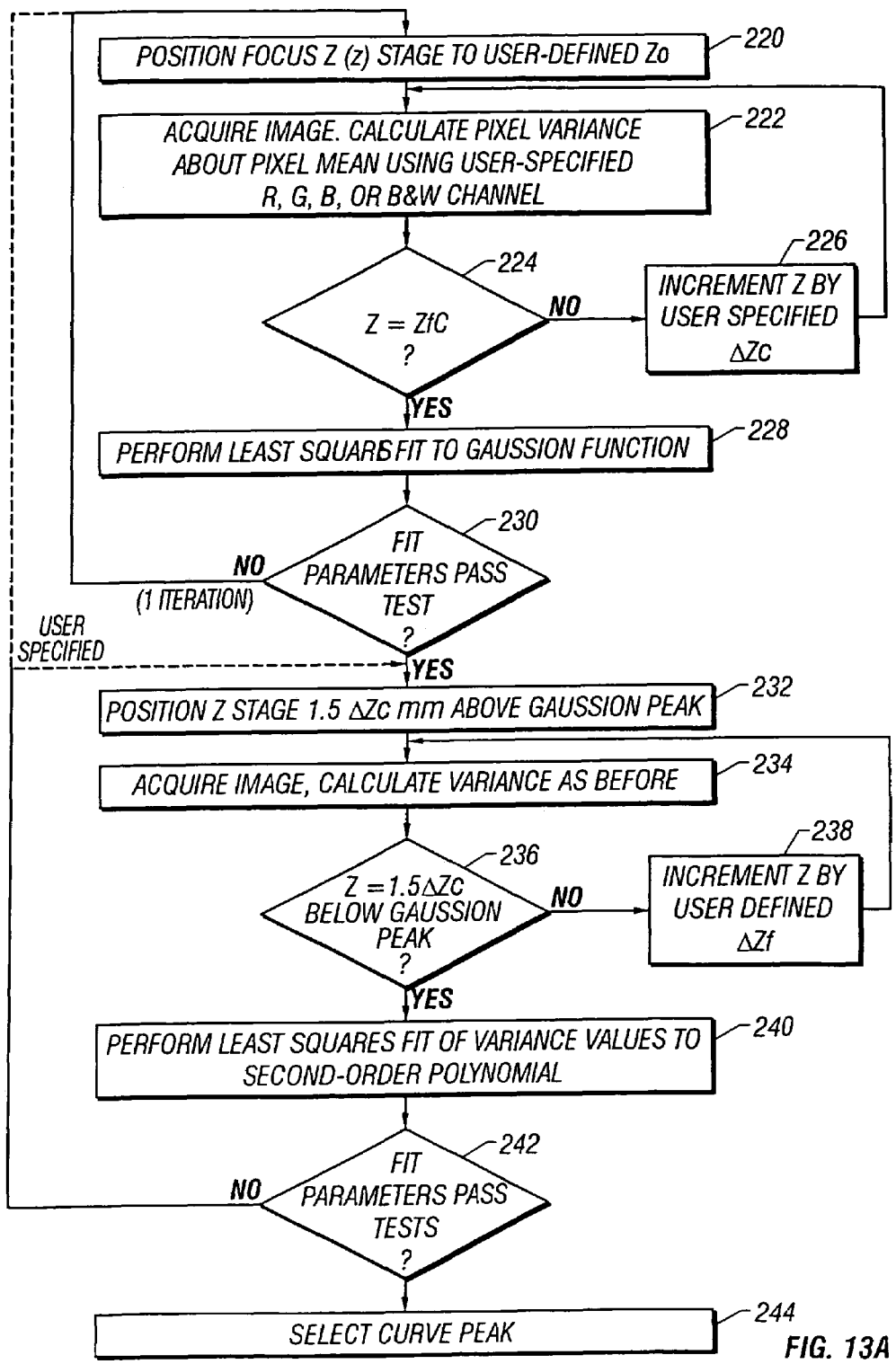
FIG. 13a is a flow diagram of a generally preferred procedure for determining a focal position.

FIG. 13*a* provides a flow diagram describing the "focus point" procedure. The basic method relies on the fact that the pixel value variance (or standard deviation) taken about the pixel value mean is maximum at best focus. A "brute-force" method could simply step through focus, using the computer controlled Z or focus stage, calculate the pixel variance at each step, and return to the focus position providing the maximum variance. Such a method would be too time consuming. Therefore, additional features were added as shown in FIG. 13*a*.

These features include the determination of pixel variance at a relatively coarse number of focal positions, and then the fitting of a curve to the data to provide a faster means of determining optimal focus. This basic process is applied in two steps, coarse and fine.

During the coarse step at 220-230, the Z stage is stepped over a user-specified range of focus positions, with step sizes that are also user-specified. For coarse focusing, these data are a close fit to a Gaussian function. Therefore, this initial set of variance versus focus position data are least-squares fit to a Gaussian function at 228. The location of the peak of this Gaussian curve determines the initial or coarse estimate of focus position for input to step 232.

A second stepping operation 230-242 is performed utilizing smaller steps over a smaller focus range centered on the coarse focus position. Experience indicates that data taken over this smaller range are generally best fit by a second order polynomial. Once this least squares fit is performed at 240, the peak of the second order curve provides the fine focus position at 244.

Figure 14:
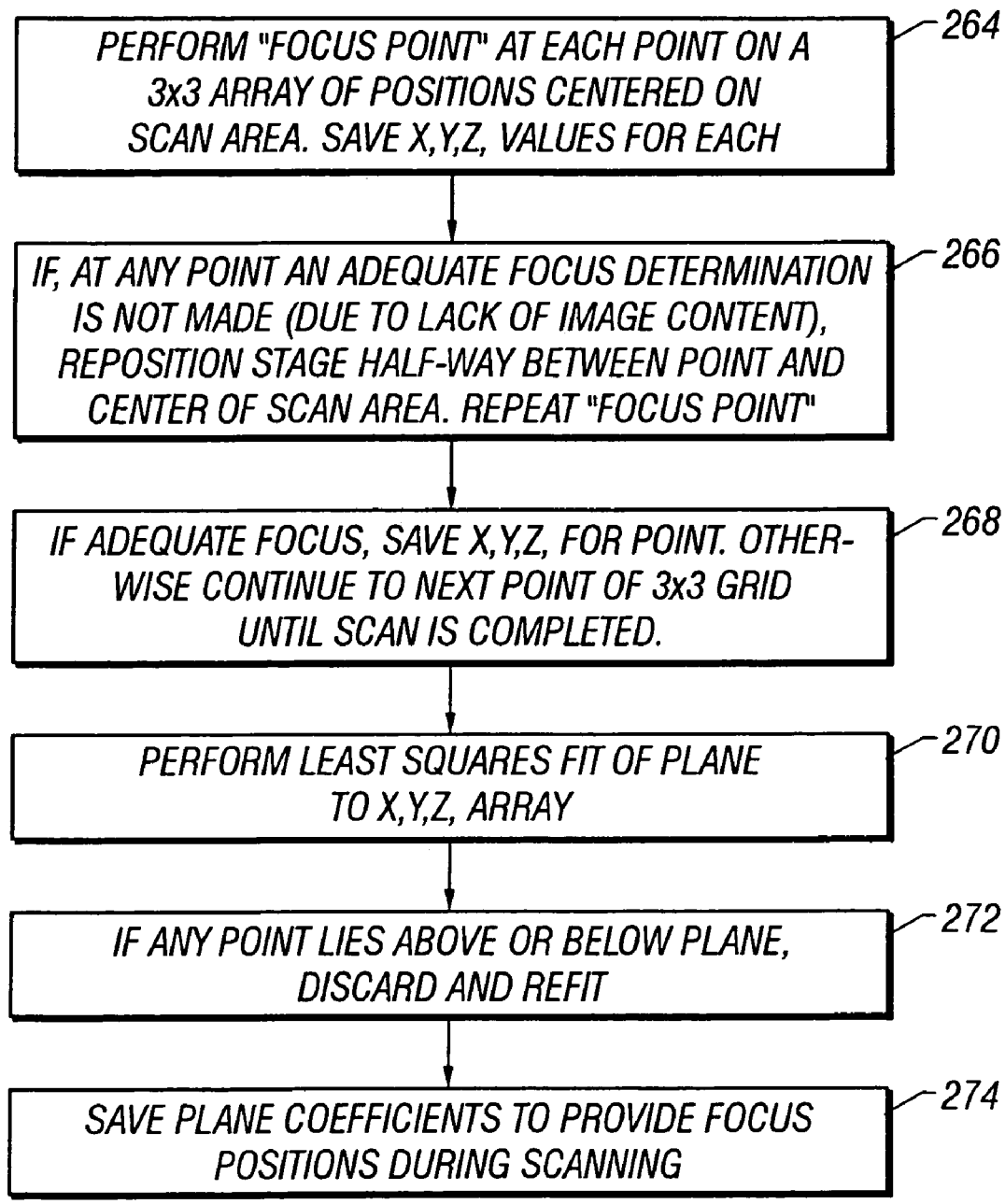
FIG. 14 is a flow diagram of a procedure for automatically determining initial focus.
Figure 15:
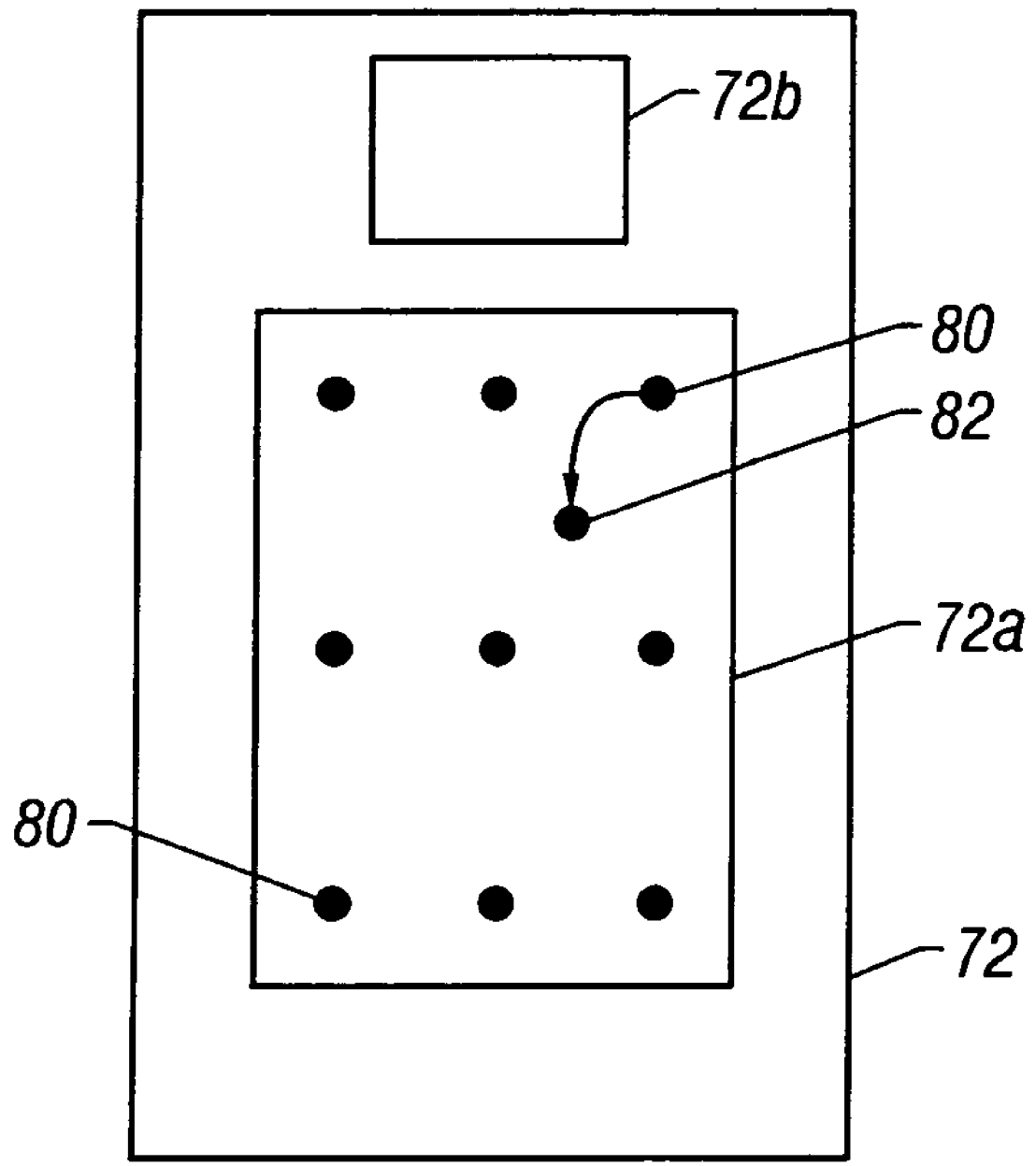
FIG. 15 shows an array of slide positions for use in the procedure of FIG. 14.

FIG. 14 illustrates a procedure for how this focusing method is utilized to determine the orientation of a slide in the carrier. As shown, focus positions are determined, as described above, for a fixed grid of points centered on the scan area at 254. Should one or more of these points lie outside the scan area, the method senses this at 266 by venue of low values of pixel variance. In this case, additional points are selected closer to the center of the scan area. FIG. 15 shows the initial array of points 80 and new point 89 selected closer to the center. Once this array of focus positions is determined at 268, a least squares plane is fit to this data at 270. Focus points lying too far above or below this best-fit plane are discarded at 272 (such as can occur from a dirty cover glass over the scan area), and the data is then refit. This plane at 274 then provides the desired Z position information for maintaining focus during scanning.

After determination of the best-fit focus plane, the scan area is scanned in an X raster scan over the scan area as described earlier. During scanning, the X stage is positioned to the starting point of the scan area, the focus (Z) stage is positioned to the best fit focus plane, an image is acquired and processed as described later, and this process is repeated for all points over the scan area. In this way, focus is maintained automatically without the need for time-consuming refocusing at points during scanning.

Figure 16:
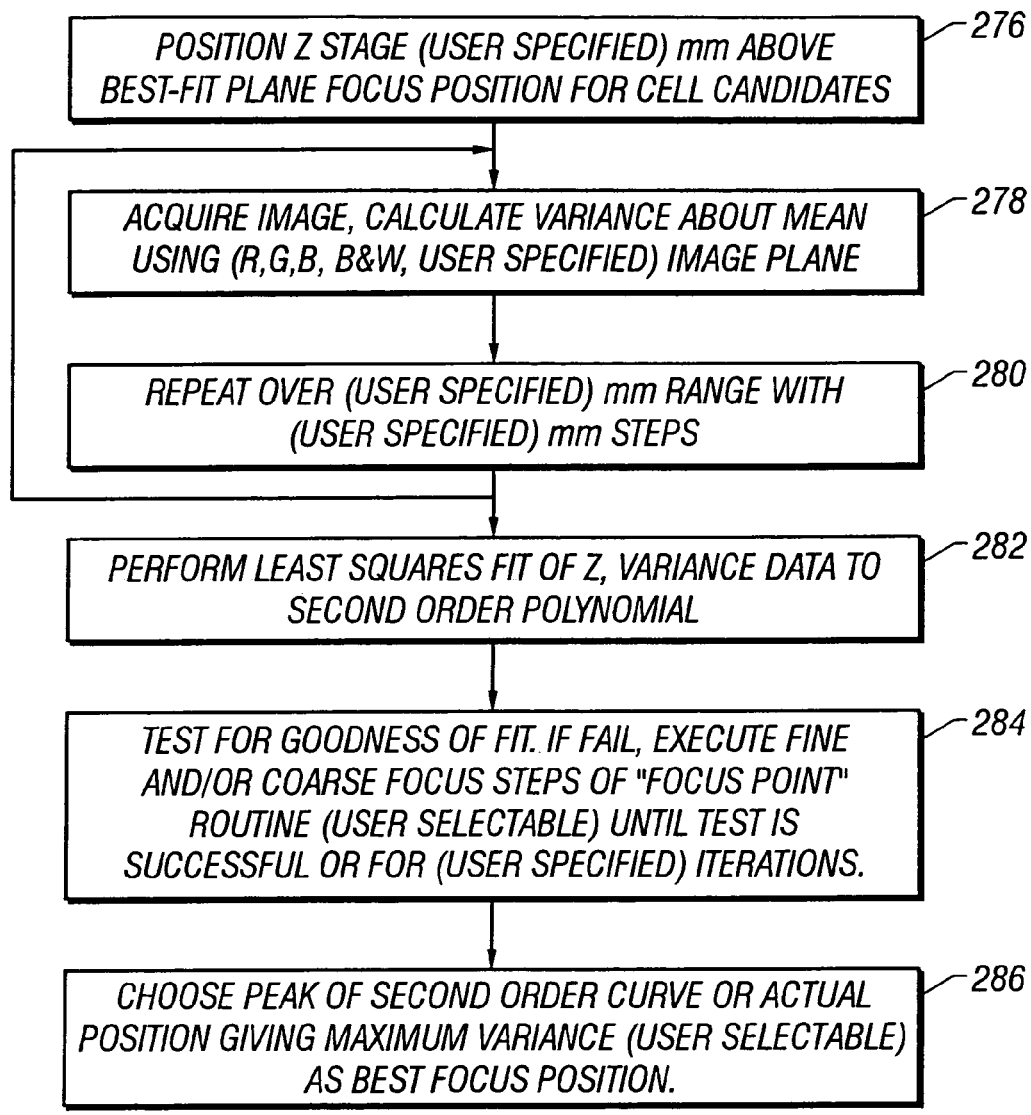
FIG. 16 is a flow diagram of a procedure for automatic focusing at a high magnification.

Prior to confirmation of cell objects at a 40× or 60× level, a refocusing operation is conducted, since the use of this higher magnification requires more precise focus than the best-fit plane provides. FIG. 16 provides the flow diagram for this process. As may be seen, this process is similar to the fine focus method described earlier in that the object is to maximize the image pixel variance. This process is accomplished by stepping through a range of focus positions with the Z stage at 276, 278, calculating the image variance at each position at 278, fitting a second order polynomial to these data at 282, and calculating the peak of this curve to yield an estimate of the best focus position at 284, 286. This final focusing step differs from previous ones in that the focus range and focus step sizes are smaller since this magnification requires focus settings to within 0.5 micron or better.

For some combinations of cell staining characteristics, improved focus can be obtained by numerically selecting the focus position that provides the largest variance, as opposed to selecting the peak of the polynomial. In such cases, the polynomial is used to provide an estimate of best focus, and a final step selects the actual Z position giving highest pixel variance. Also, if at any time during the focusing process at 40× or 60× the parameters indicate that the focus position is inadequate, the system automatically reverts to a coarse focusing process as described above with reference to FIG. 13A. This ensures that variations in subsample thickness can be accommodated in an expeditious manner.

For some cellular specimens and stains, the focusing methods discussed above do not provide optimal focused results. For example, certain white blood cells known as neutrophils may be stained with Fast Red, a commonly known stain, to identify alkaline phosphatase in the cytoplasm of the cells. To further identify these cells and the material within them, the specimen may be counterstained with hematoxylin to identify the nucleus of the cells. In cells so treated, the cytoplasm bearing alkaline phosphatase becomes a shade of red proportionate to the amount of alkaline phosphatase in the cytoplasm and the nucleus becomes blue. However, where the cytoplasm and nucleus overlap, the cell appears purple.

Figure 13B:
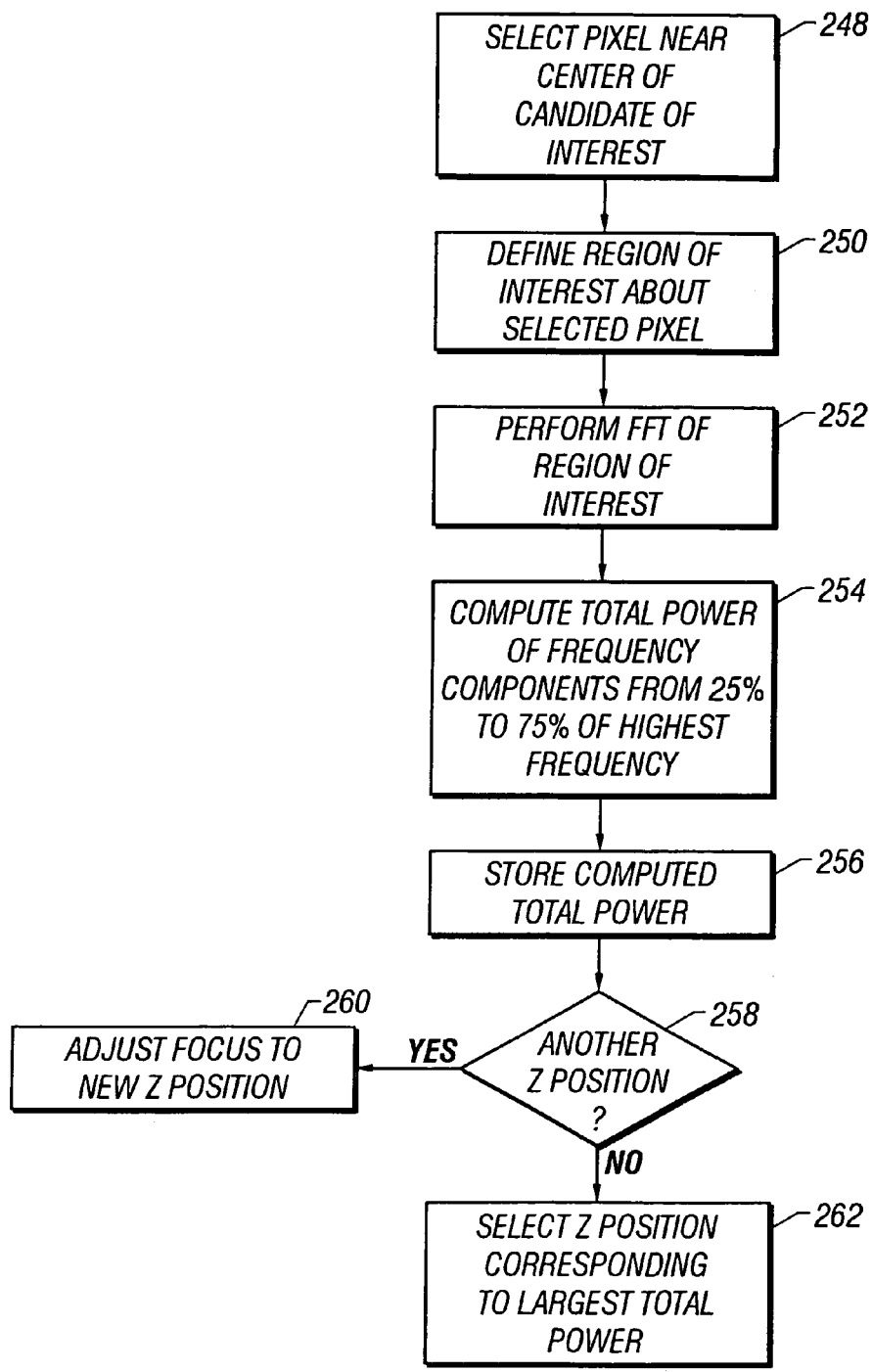
FIG. 13b is a flow diagram of a preferred procedure for determining a focal position for neutrophils stained with Fast Red and counter-stained with hematoxylin.

To find a best focal position at high magnification, a focus method, such as the one shown in FIG. 13$b$, may be used. That method begins by selecting a pixel near the center of a candidate object of interest (Block 248) and defining a region of interest centered about the selected pixel (Block 250). Preferably, the width of the region of interest is a number of columns which is a power of 2. This width preference arises from subsequent processing of the region of newest preferably using a one dimensional Fast Fourier Transform (FFT) technique. As is well known in the art, processing columns of pixel values using the FFT technique is facilitated by making the number of columns to be processed a power of two, while the height of the region of interest is also a power of two in the preferred embodiment, it need not be unless a two dimensional FFT technique is used to process the region of interest.

After the region of interest is selected, the columns of pixel values are processed using the preferred one dimensional FFT to determine a spectra of frequency components for the region of interest (Block 252). The frequency spectra ranges from DC to some highest frequency component. For each frequency component, a complex magnitude is computed. Preferably, the complex magnitudes for the frequency components which range from approximately 25% of the highest component to approximately 75% of the highest component are squared and slimmed to determine the total power for the region of interest (Block 254). Alternatively, the region of interest may be processed with a smoothing window, such as a Hanning window, to reduce the spurious high frequency components generated by the FFT processing of the pixel values in the region of interest. Such preprocessing of the region of interest permits all complex magnitude over the complete frequency range to be squared and summed. After the power for a region has been computed and stored (Block 256), a new focal position is selected, focus adjusted (Blocks 258, 260), and the process repeated. After each focal position has been evaluated, the one having the greatest power factor is selected as the one best in focus (Block 262).

The following describes the image processing methods which are utilized to decide whether a candidate object of interest, such as a stained cell, is present in a given image, or field, during the scanning process. Candidate objects of interest which are detected during scanning are reimaged at higher (40× or 60×) magnification, the decision confirmed, and a region of interest for this cell saved for later review by the pathologist.

The image processing includes color space conversion, low pass filtering, background suppression, artifact suppression, morphological processing, and blob analysis. One or more of these steps can optionally be eliminated. The operator is provided with an option to configure the system to perform any or all of these steps and whether to perform certain steps more than once or several times in a row. The sequence of steps can be varied and thereby optimized for specific reagents or reagent combinations; however, the sequence described herein is preferred. The image processing steps of low pass filtering, thresholding, morphological processing, and blob analysis are generally known image processing building blocks.

Figure 17A:
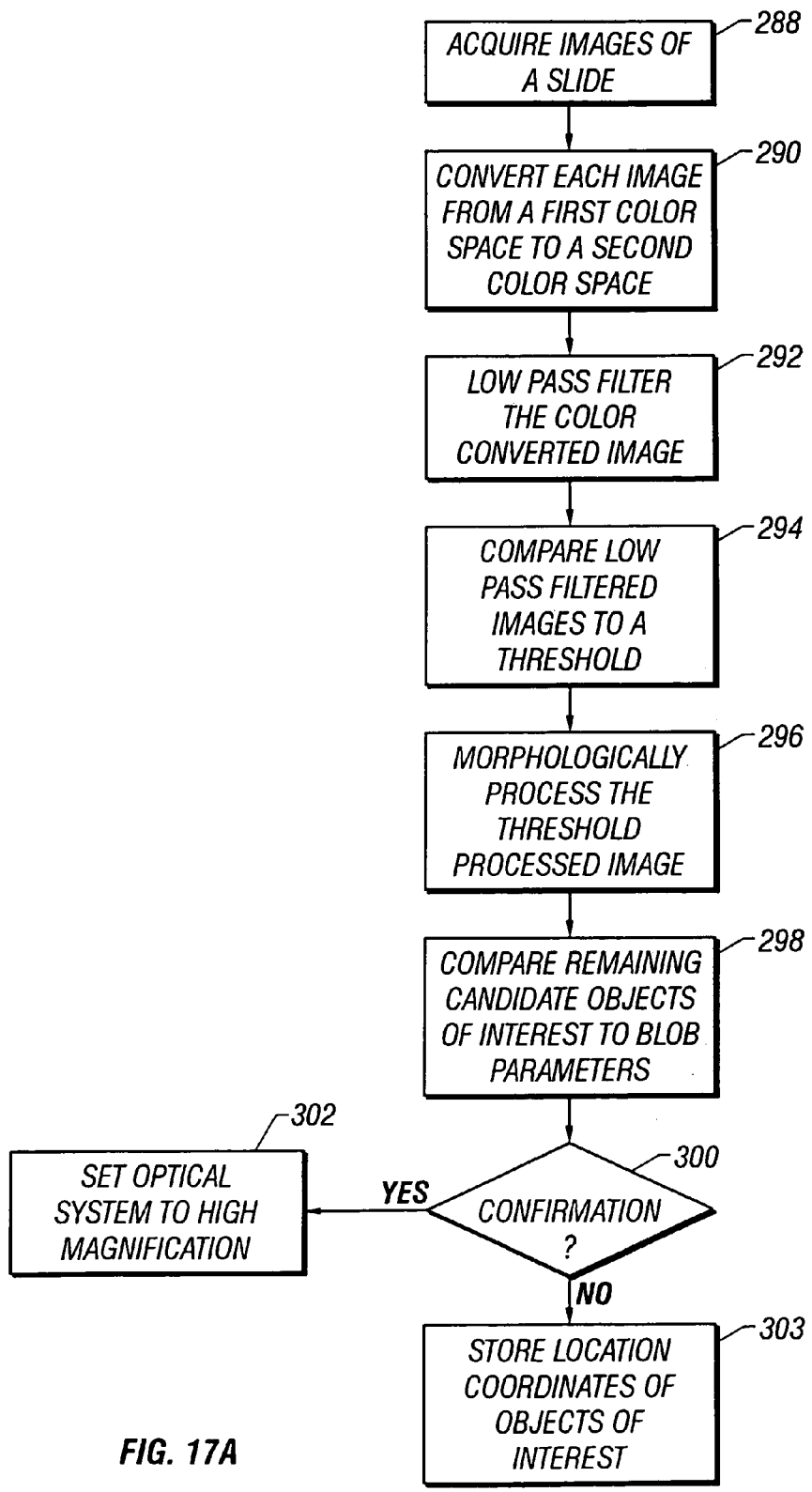
FIG. 17a is a flow diagram of an overview of the preferred process to locate and identify objects of interest in a stained cellular specimen on a slide.

An overview of the preferred process is shown in FIG. 17a. The preferred process for identifying and locating candidate objects of interest in a stained subsample on a slide begins with an acquisition of images obtained by scanning the slide at low magnification (Block 288). Each image is then converted from a first color space to a second color space (Block 290) and the color converted image is low pass filtered (Block 292). The pixels of the low pass filtered image are then compared to a threshold (Block 994) and, preferably, those pixels having a value equal to or greater than the threshold are identified as candidate object of interest pixels and those less than the threshold are determined to be artifact or background pixels. The candidate object of interest pixels are then morphologically processed to identify groups of candidate object of interest pixels as candidate objects of interest (Block 296). These candidate objects of interest are then compared to blob analysis parameters (Block 298) to further differentiate candidate objects of interest from objects which do not conform to the blob analysis parameters and, thus, do not warrant further processing. The location of the candidate objects of interest may be stored prior to confirmation at high magnification. The process continues by determining whether the candidate objects of interest have been confirmed (Block 300). If they have not been determined, the optical system is set to high magnification (Block 302) and images of the slide at the locations corresponding to the candidate objects of interest identified in the low magnification images are acquired (Block 288). These images are then color converted (Block 290), low pass filtered (Block 292), compared to a threshold (Block 294), morphologically processed (Block 296), and compared to blob analysis parameters (Block 298) to confirm which candidate objects of interest located from the low magnification images are objects of interest. The coordinates of the objects of interest are then stored for future reference (Block 303).

In general, the candidate objects of interest, such as stained cells, are detected based on a combination of characteristics, including size, shape, and color. The chain of decision making based on these characteristics preferably begins with a color space conversion process. A camera, preferably a CCD camera, coupled to the microscope subsystem outputs a color image comprising a matrix of 640× 480 pixels. Each pixel comprises red, green and blue (RGB) signal values.

It is desirable to transform the matrix of RGB values to a different color space because the difference between candidate objects of interest and their background, such as stained cells, may be determined from their respective colors. Subsamples are generally stained with one or more industry standard stains (e.g., DAB, New Fuchsin, AEC) which are "reddish" in color. Candidate objects of interest retain more of the stain and thus appear red while normal cells remain unstained. The subsamples may also be counter-stained with hematoxylin so the nuclei of normal cells or cells not containing an object of interest appear blue. In addition to these objects, dirt and debris can appear as black, gray, or can also be lightly stained red or blue depending on the staining procedures utilized. The residual plasma or other fluids also present on a smear may also possess some color.

In the color conversion operation, a ratio of two of the RGB signal values is formed to provide a means for discriminating color information. With three signal values for each pixel, nine different ratios can be formed:

R/R, R/G, R/B, G/G, G/B, G/R, B/B, B/G, B/R where R is red, G is green, and B is red.

The optimal ratio to select depends upon the range of color information expected in the subsample. As noted above, typical stains used for detecting candidate objects of interest are predominantly red, as opposed to predominantly green or blue. Thus, the pixels of a cell of interest which has been stained contain a red component which is larger than either the green or blue components. A ratio of red divided by blue (R/B) provides a value which is greater than one for stained cells but is approximately one for any clear or white areas on the slide. Since the remaining cells, i.e., normal cells, typically are stained blue, the R/B ratio for pixels of these latter cells yields values of less than one. The R/B ratio is preferred for clearly separating the color information typical in these applications.

Figure 17B:
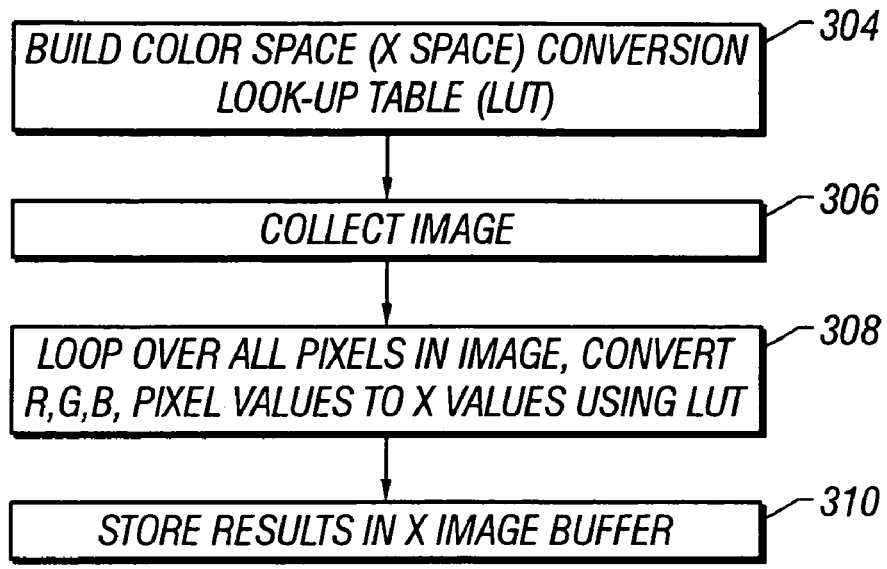
FIG. 17b is a flow diagram of a procedure for color space conversion.

FIG. 17b illustrates the flow diagram by which this conversion is performed. In the interest of processing speed, the conversion is implemented with a look-up-table. The use of a look up table for color conversion accomplishes three functions: (1) performing a division operation; (2) scaling the result for processing as an image having pixel values ranging from 0 to 255; and (3) defining objects that have low pixel values in each color band (R,G,B) as "black" to avoid infinite ratios (i.e., dividing by zero). These "black" objects are typically stalking artifacts or can be edges of bubbles caused by pasting a cover glass over the subsample.

Once the look-up-table 304 is built for the specific color ratio (i.e., choices of cell stains), each pixel in the original RGB image is converted at 308 to produce the output. In this way, the desired objects of interest can be numerically discriminated. The resulting 640×480 pixel matrix, referred to as the X-image, is a gray scale image having values ranging from 0 to 255.

Other methods exist for discriminating color information. One classical method converts the RGB color information into another color space, such as HSI (hue, saturation, intensity) space. In such a space, distinctly different hues such as red, blue, green, yellow, may be readily separated. In addition, relatively lightly stained objects may be distinguished from more intensely stained ones by virtue of differing saturations. However, converting from RGB space to HSI space requires more complex computation. Conversion to a color ratio is faster; for example, a full image can be converted by the ratio technique of the present invention in about 10 ms while an HSI conversion can take several seconds.

In yet another approach, one could obtain color information by taking a single color channel from the camera. As an example, consider a blue channel, in which objects that are red are relatively dark. Objects which are blue, or white, are relatively light in the blue channel. In principle, one could take a single color channel, and simply set a threshold wherein everything darker than some threshold is categorized as a candidate object of interest, for example, a stained cell, because it is red and hence dark in the channel being reviewed. However, one problem with the single channel approach occurs where illumination is not uniform. Non-uniformity of illumination results in non-uniformity across the pixel values in any color channel, for example, tending to peak in the middle of the image and dropping off at the edges where the illumination falls off. Performing thresholding on this non-uniform color information runs into problems, as the edges sometimes fall below the threshold, and therefore it becomes more difficult to pick the appropriate threshold level. However, with the ratio technique, if the values of the red channel fall off from center to edge, then the values of the blue channel also fall off center to edge, resulting in a uniform ratio. Thus, the ratio technique is more immune to illumination non-uniformities.

As previously described, the color conversion scheme is relatively insensitive to changes in color balance, i.e., the relative outputs of the red, green, and blue channels. However, some control is necessary to avoid camera saturation, or inadequate exposures in any one of the color bands. This color balancing is performed automatically by utilizing a calibration slide consisting of a clear area, and a "dark" area having a known optical transmission or density. The system obtains images from the clear and "dark" areas, calculates "white" and "black" adjustments for the image processor 25, and thereby provides correct color balance.

In addition to the color balance control, certain mechanical alignments are automated in this process. The center point in the field of view for the various microscope objectives as measured on the slide can vary by several (or several tens of) microns. This results from slight variations in position of the microscope objectives 44a as determined by the turret 44 (FIG. 4), small variations in alignment of the objectives with respect to the system optical axis, and other factors. Since it is desired that each microscope objective be centered at the same point, these mechanical offsets must be measured and automatically compensated.

This compensation is accomplished by imaging a test slide which contains a recognizable feature or mark. An image of this pattern is obtained by the system with a given objective, and the position of the mark determined. The system then rotates the turret to the next lens objective, obtains an image of the test object, and its position is redetermined. Apparent changes in position of the test mark are recorded for this objective. This process is continued for all objectives.

Once these spatial offsets have been determined, they are automatically compensated for by moving the stage 38 by an equal (but opposite) amount of offset during changes in objective. In this way, as different lens objectives are selected, there is no apparent strife in center point or area viewed.

A low pass filtering process precedes thresholding. An objective of thresholding is to obtain a pixel image matrix having only candidate objects of interest, such as stained cells above a threshold level and everything else below it. However, an actual acquired image contains noise. The noise can take several forms, including white noise and artifacts. The microscope slide can have small fragments of debris that pick up color in the staining process and these are known as artifacts. These artifacts are generally small and scattered areas, on the order of a few pixels, which are above the threshold. The purpose of low pass filtering is to essentially blur or smear the entire color converted image. The low pass filtering process smears artifacts more than larger objects of interest, and thereby eliminate or reduce the number of artifacts that pass the thresholding process. The result is a cleaner thresholded image downstream.

In the low pass filter process, a 3×3 matrix of coefficients is applied to each pixel in the 640×480 x-image. A preferred coefficient matrix is as follows:

$$\begin{bmatrix} 1/9 & 1/9 & 1/9 \\ 1/9 & 1/9 & 1/9 \\ 1/9 & 1/9 & 1/9 \end{bmatrix}$$

At each pixel location, a 3×3 matrix comprising the pixel of interest and its neighbors is multiplied by the coefficient matrix and summed to yield a single value for the pixel of interest.

The output of this spatial convolution process is again a 640×480 matrix.

As an example, consider a case where the center pixel and only the center pixel, has a value of 255 and each of its other neighbors, top left, top, top right and so forth, have values of 0. This singular white pixel case corresponds to a small object. The result of the matrix multiplication and addition using the coefficient matrix is a value of 1/9 (255) or 28 for the center pixel, a value which is below the nominal threshold of 128. Now consider another case in which all the pixels have a value of 255 corresponding to a large object. Performing the low pass filtering operation on a 3×3 matrix for this case yields a value of 255 for the center pixel. Thus, large objects retain their values while small objects are reduced in amplitude or eliminated. In the preferred method of operation, the low pass filtering process is performed on the X image twice in succession.

To separate objects of interest, a thresholding operation is performed designed to set pixels within cells of interest to a value of 255, and all other areas to 0. Thresholding ideally yields an image in which cells of interest are white and the remainder of the image is black. A problem one faces in thresholding is where to set the threshold level. One cannot simply assume that cells of interest are indicated by any pixel value above the nominal threshold of 128. A typical imaging system may use an incandescent halogen light bulb as a light source. As the bulb ages, the relative amounts of red and blue output can change. The tendency as the bulb ages is for the blue to drop off more than the red and the green. To accommodate for this light source variation over time, a dynamic thresholding process is used whereby the threshold is adjusted dynamically for each acquired image. Thus, for each 640×480 image, a single threshold value is derived specific to that image.

Figure 18:
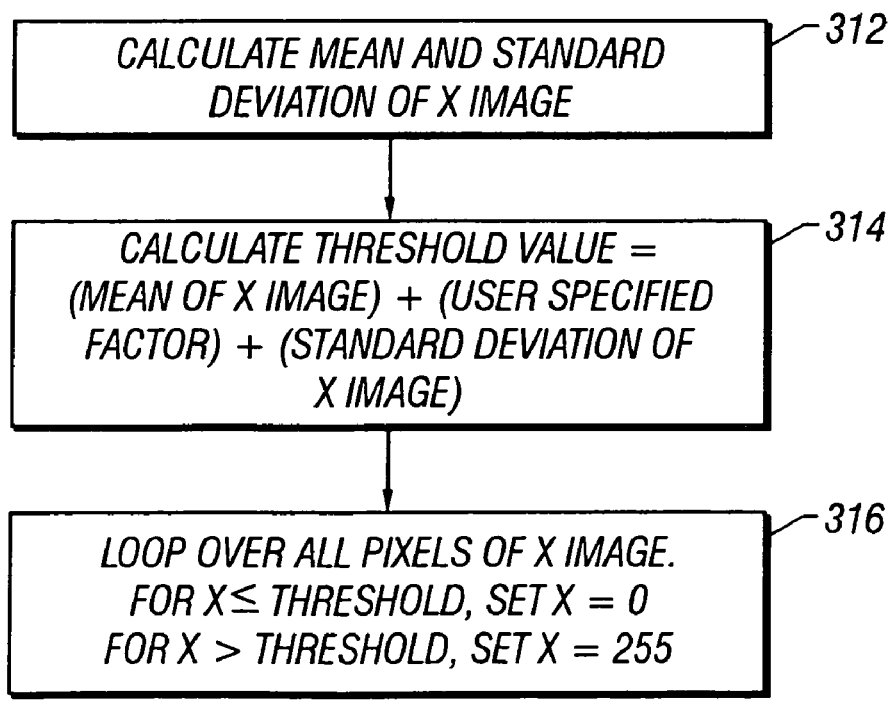
FIG. 18 is a flow diagram of a procedure for background suppression by dynamic thresholding.

As shown in FIG. 18, the basic method is to calculate, for each field, the mean X value, and the standard deviation about this mean at 312. The threshold is then set at 314 to the mean plus an amount defined by the product of a (user specified) factor and the standard deviation of the color converted pixel values. The standard deviation correlates to the structure and number of objects in the image. Preferably, the user specified factor is in the range of approximately 1.5 to 2.5. The factor is selected to be in the lower end of the range for slides in which the stain has primarily remained within cell boundaries and the factor is selected to be in the upper end of the range for slides in which the stain is pervasively present throughout the slide. In this way, as areas are encountered on the slide with greater or lower background intensities, the threshold may be raised or lowered to help reduce background objects. With this method, the threshold changes in step with the aging of the light source such that the effects of the aging are canceled out. The image matrix resulting at 316 from the thresholding step is a binary image of black (0) and white (255) pixels.

As is often the case with thresholding operations such as that described above, some undesired areas lies above the threshold value due to noise, small stained cell fragments, and other artifacts. It is desired and possible to eliminate these artifacts by virtue of their small size compared with legitimate cells of interest. Morphological processes are utilized to perform this function.

Morphological processing is similar to the low pass filter convolution process described earlier except that it is applied to a binary image. Similar to spatial convolution, the morphological process traverses an input image matrix, pixel by pixel, and places the processed pixels in an output matrix. Rather than calculating a weighted sum of neighboring pixels as in the low pass convolution process, the morphological process uses set theory operations to combine neighboring pixels in a nonlinear fashion.

Erosion is a process whereby a single pixel layer is taken away from the edge of an object. Dilation is the opposite process which adds a single pixel layer to the edges of an object. Fine power of morphological processing is that it provides for further discrimination to eliminate small objects that have survived the thresholding process and yet are not likely the cells of interest. The erosion and dilation processes that make up a morphological "open" preferably make small objects disappear yet allows large objects to remain. Morphological processing of binary images is described in detail in *Digital Image Processing* (G. A. Saxes, John Wiley & Sons, 1994, pp. 127-137).

Figure 19:
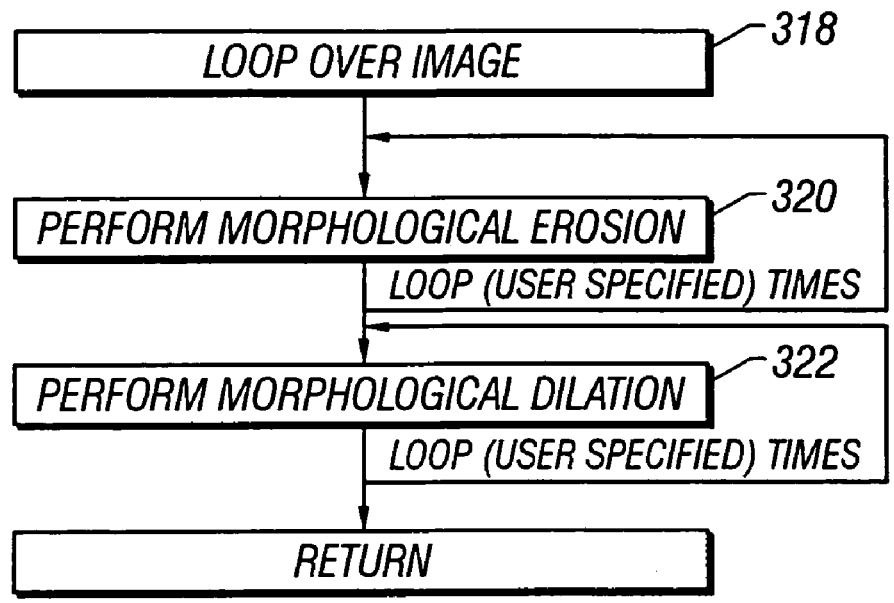
FIG. 19 is a flow diagram of a procedure for morphological processing.

FIG. 19 illustrates the flow diagram for this process. As shown here, a morphological "open" process performs this suppression. A single morphological open consists of a single morphological erosion 320 followed by a single morphological dilation 322. Multiple "opens" consist of multiple erosions by multiple dilations. In the preferred embodiment, one or two morphological opens are found to be suitable.

At this point in the processing chain, the processed image contains thresholded objects of interest, such as stained cells (if any were present in the original image), and possibly some residual artifacts that were too large to be eliminated by the processes above.

Figure 20:
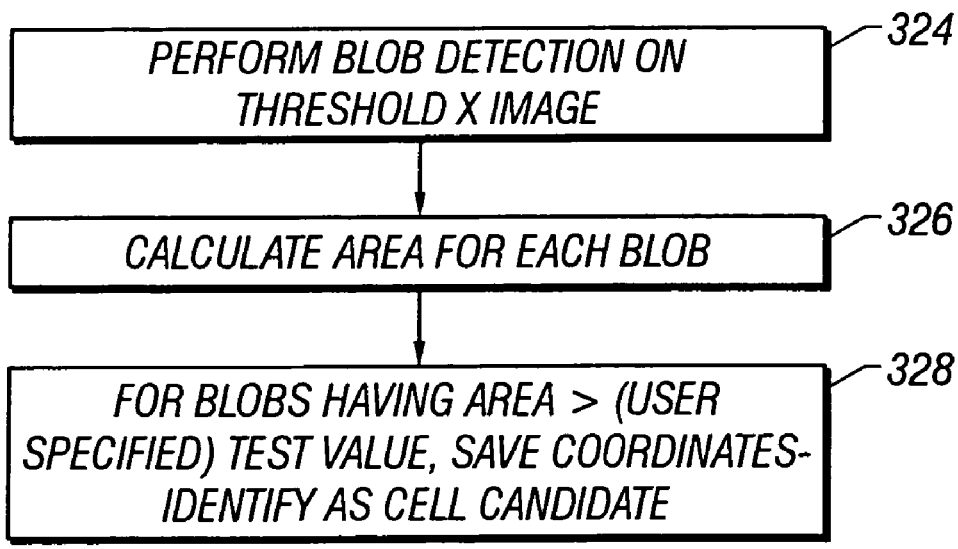
FIG. 20 is a flow diagram of a procedure for blob analysis.

FIG. 20 provides a flow diagram illustrating a blob analysis performed to determine the number, size, and location of objects in the thresholded image. A blob is defined as a region of connected pixels having the same "color", in this case, a value of 255. Processing is performed over the entire image to determine the number of such regions at 324 and to determine the area and x,y coordinates for each detected blob at 326.

Comparison of the size of each blob to a known determined area at 328 for a stained cell allows a refinement in decisions about which objects are objects of interest, such as stained cells, and which are artifacts. The location (x,y coordinates) of objects identified as cells of interest in this stage are saved for the final 40× reimaging step described below. Objects not passing the size test are disregarded as artifacts.

Figure 21:
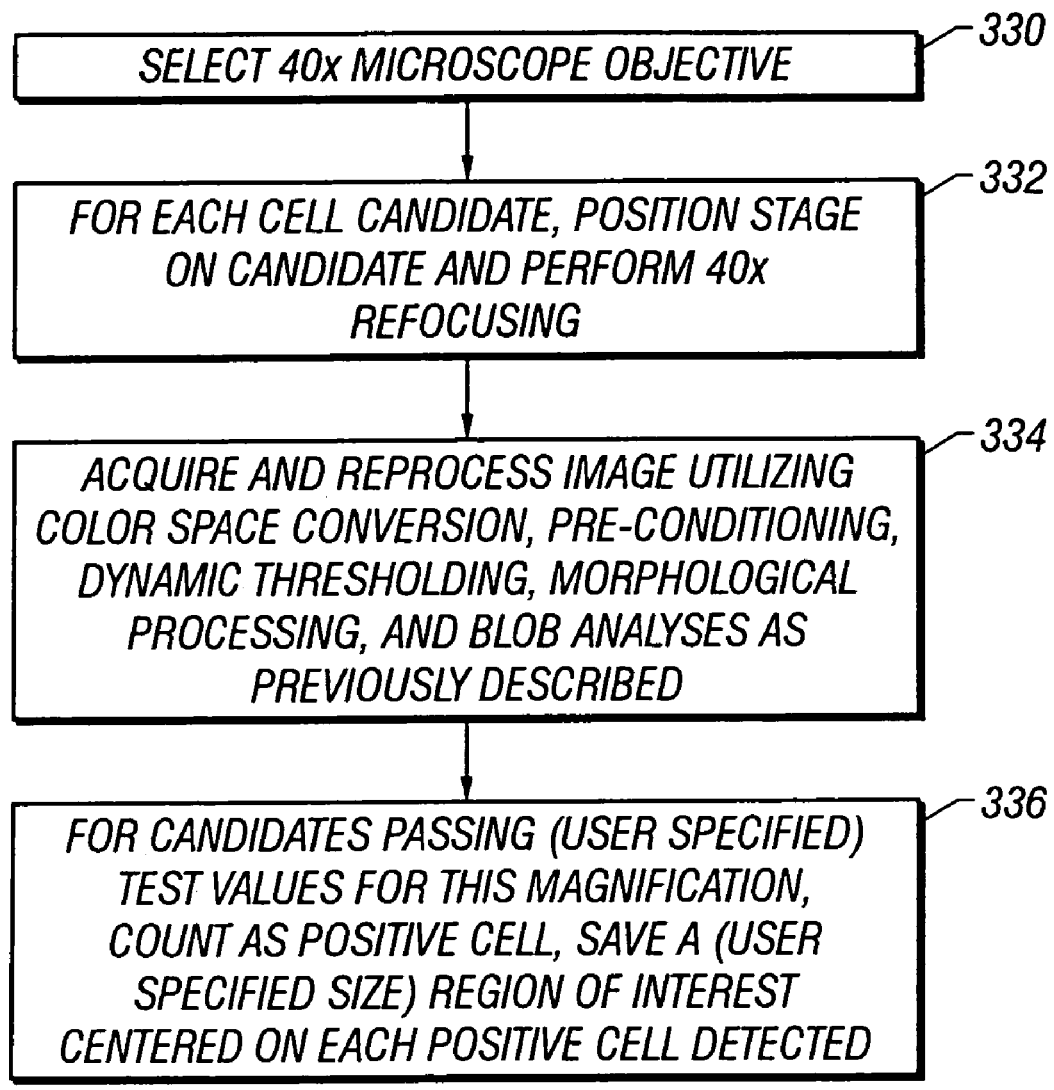
FIG. 21 is a flow diagram of a procedure for image processing at a high magnification.

The processing chain described above identifies objects at the scanning magnification as cells of interest candidates. As illustrated in FIG. 21, at the completion of scanning the system switches to the 40× magnification objective at 330, and each candidate is reimaged to confirm the identification 332. Each 40× image is reprocessed at 334 using the same steps as described above but with test parameters suitably modified for the higher magnification (e.g., area). At 336, a region of interest centered on each confirmed cell is saved to the hard drive for review by the pathologist.

Figure 22:
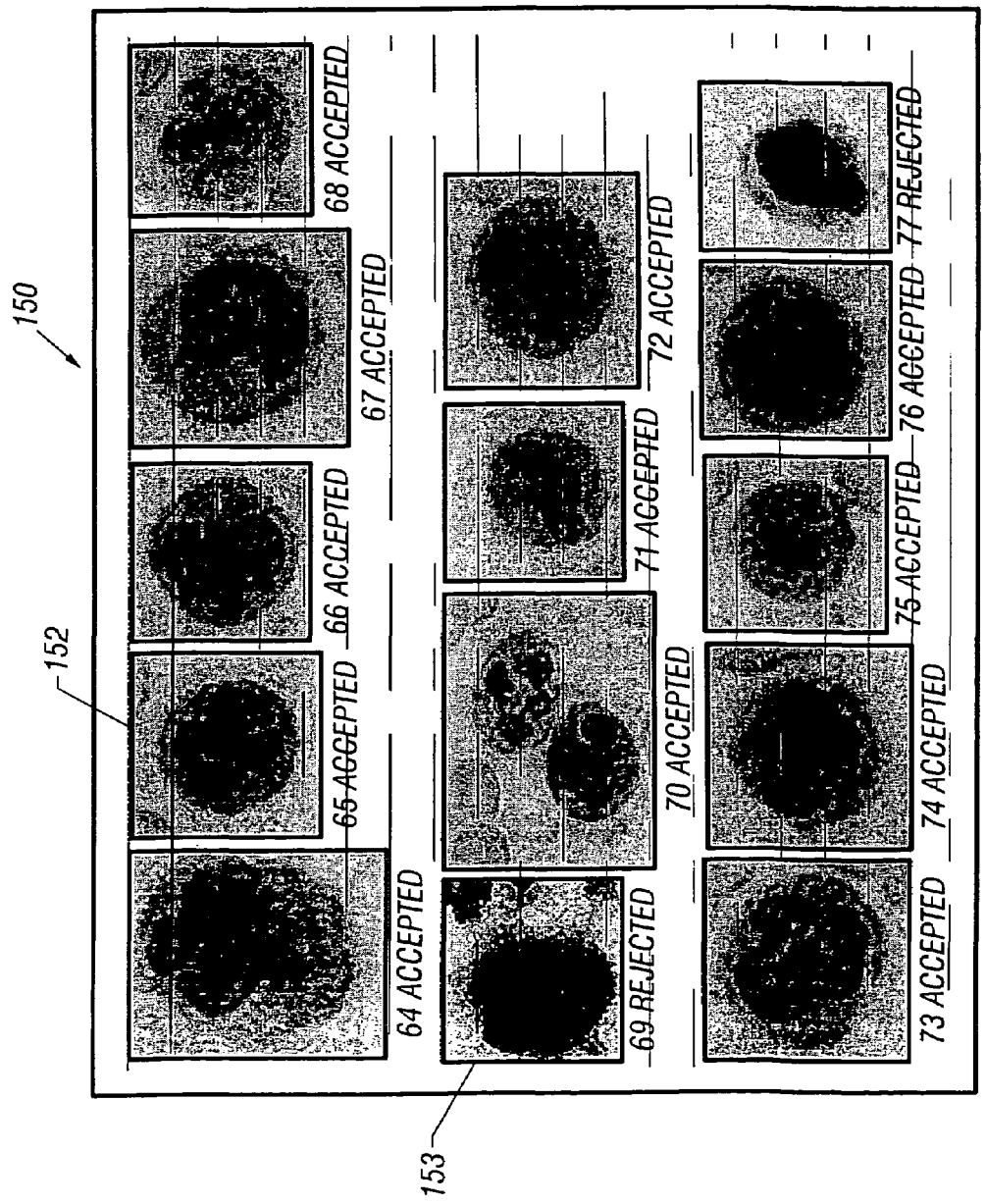
FIG. 22 illustrates a mosaic of cell images produced by the apparatus.

As noted earlier, a mosaic of saved images is made available for viewing by the pathologist. As shown in FIG. 22, a series of images of cells which have been confirmed by the image analysis is presented in the mosaic 150. The pathologist can then visually inspect the images to make a determination whether to accept (152) or reject (153) each cell image. Such a determination can be noted and saved with the mosaic of images for generating a printed report.

In addition to saving the image of the cell and its region, the cell coordinates are saved should the pathologist wish to directly view the cell through the oculars or on the image monitor. In this case, the pathologist reloads the slide carrier, selects the slide and cell for review from a mosaic of cell images, and the system automatically positions the cell under the microscope for viewing.

Figure 23:
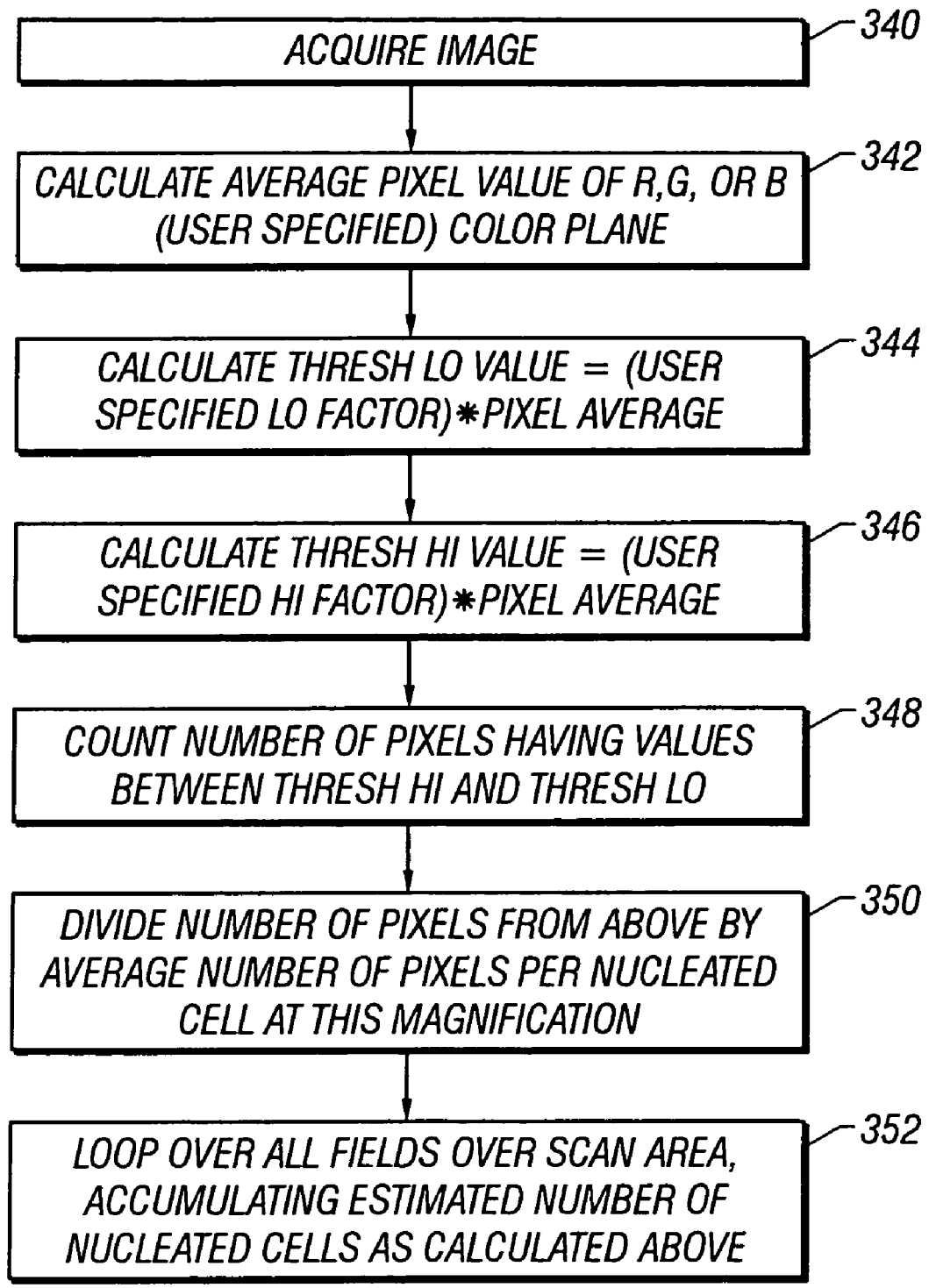
FIG. 23 is a flow diagram of a procedure for estimating the number of nucleated cells in a scan area.

Normal cells whose nuclei have been stained with hematoxylin are often quite numerous, numbering in the thousands per 10× image. Since these cells are so numerous, and since they tend to clump, counting each individual nucleated cell would add an excessive processing burden, at the expense of speed, and would not necessarily provide an accurate count due to clumping. The apparatus performs an estimation process in which the total area of each field that is stained hematoxylin blue is measured and this area is divided by the average size of a nucleated cell. FIG. 23 outlines this process.

In this process, a single color band (the red channel provides the best contrast for blue stained nucleated cells) is processed by calculating the average pixel value for each field at 342, establishing two threshold values (high and low) as indicated at 334, 346, and counting the number of pixels between these two values at 348. In the absence of dirt, or other opaque debris, this provides a count of the number of predominantly blue pixels. By dividing this value by the average area for a nucleated cell at 350, and looping over all fields at 352, an approximate cell count is obtained. Preliminary testing of this process indicates an accuracy with +/−15%. For some slide preparation techniques, the size of nucleated cells can be significantly larger than the typical size. The operator can select the appropriate nucleated cell size to compensate for these characteristics.

As with any imaging system, there is some loss of modulation transfer (i.e., contrast) due to the modulation transfer function (MTF) characteristics of the imaging optics; camera, electronics, and other components. Since it is desired to save "high quality" images of cells of interest both for pathologist review and for archival purposes, it is desired to compensate for these MTF losses.

An MTF compensation, or MTFC, is performed as a digital process applied to the acquired digital images. A digital filter is utilized to restore the high spatial frequency content of the images upon storage, while maintaining low noise levels. With this MTFC technology, image quality is enhanced, or restored, through the use of digital processing methods as opposed to conventional oil-immersion or other hardware based methods. MTFC is described further in *The Image Processing Handbook* (J. C. Rues, CRC Press, 1995, pp. 225 and 337).

Figure 24A:
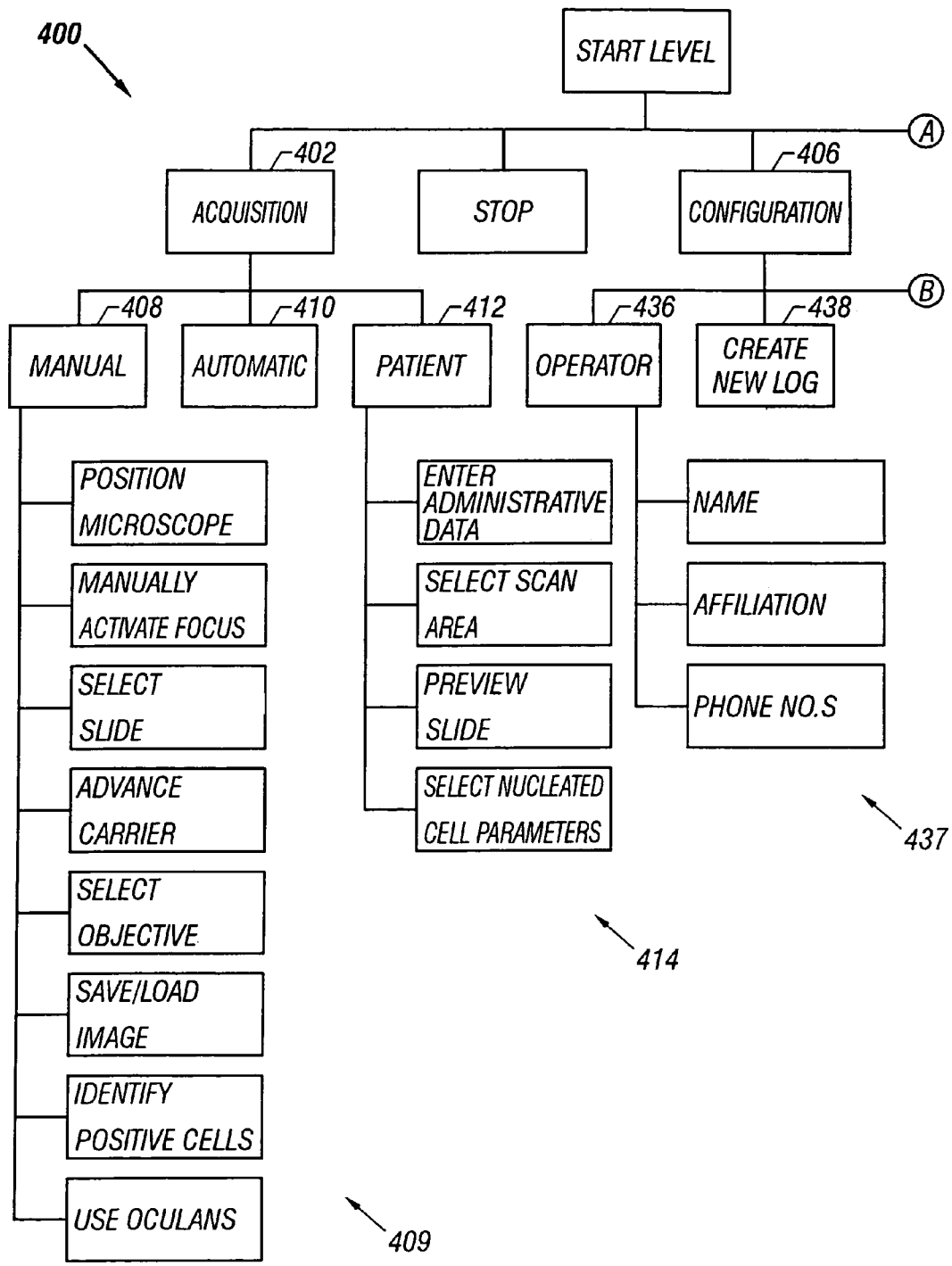
FIG. 24 illustrates the apparatus functions available in a user interface of the apparatus.
Figure 24B:
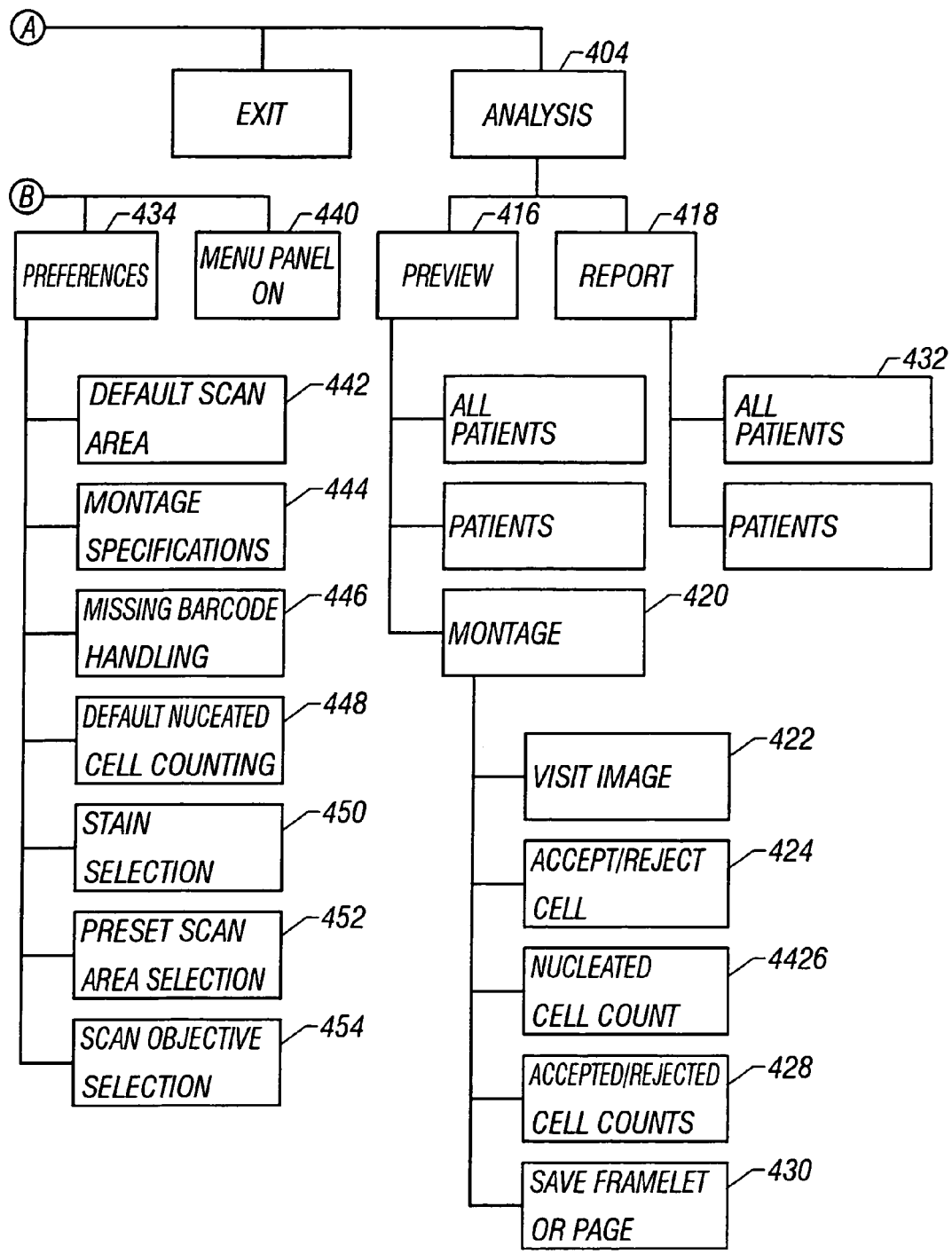

Referring to FIG. 24, the functions available in a user interface of the apparatus 10 are shown. From the user interface, which is presented graphically on computer monitor 26, an operator can select among apparatus functions which include acquisition 402, analysts 404, and system configuration 406. At the acquisition level 402, the operator can select between manual 408 and automatic 410 modes of operation. In the manual mode, the operator is presented with manual operations 409. Patient information 414 regarding an assay can be entered at 412. In the analysis level 404, review 416 and report 418 functions are made available. At the review level 416, the operator can select a montage function 420. At this montage level, a pathologist can perform diagnostic review functions including visiting an image 422, accept/reject of cells 424, nucleated cell counting 426, accept/reject of cell counts 428, and saving of pages at 430. The report level 418 allows an operator to generate patient reports 432.

In the configuration level 406, the operator can select to configure preferences at 434, input operator information 437 at 436, create a system log at 438, and toggle a menu panel at 440. The configuration preferences include scan area selection functions at 442, 452; montage specifications at 444, bar code handling at 446, default cell counting at 448, stain selection at 450, and scan objective selection at 454.

Computer Implementation

Aspects of the invention may be implemented in hardware or software, or a combination of both. However, preferably, the algorithms and processes of the invention are implemented in one or more computer programs executing on programmable computers each comprising at least one processor, at least one data storage system (including volatile and non-volatile memory and/or storage elements), at least one input device, and at least one output device. Program code is applied to input data to perform the functions described herein and generate output information. The output information is applied to one or more output devices, in known fashion.

Each program may be implemented in any desired computer language (including machine, assembly, high level procedural, or object oriented programming languages) to communicate with a computer system. In any case, the language may be a compiled or interpreted language.

Each such computer program is preferably stored on a storage media or device (e.g., ROM, CD-ROM, tape, or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

A number of embodiments of the present invention have been described. Nevertheless, various modifications may be made without departing from the spirit and scope of the invention. Accordingly, the invention is not to be limited by the specific illustrated embodiment, but only by the scope of the appended claims.

What is claimed is:

1. An automated method for the measurement of residual protein in a cellular specimen, comprising:
   (a) providing a plurality of stained subsamples from a cellular specimen;
   (b) automatically selecting a Z position in each subsample for imaging a candidate object of interest;
   (c) automatically obtaining a low magnification image of the candidate objects of interest comprising obtaining a plurality of pixels in each subsample;
   (d) automatically filtering the candidate object of interest pixels in each subsample with a low pass filter;
   (e) automatically morphologically processing the candidate object of interest pixels in each subsample to identify artifact pixels;
   (f) automatically identifying the candidate object of interest in each subsample by eliminating pixels identified as artifact pixels;
   (g) adjusting the apparatus to a higher magnification;
   (h) automatically acquiring a higher magnification image of the subsample, at the location coordinates corresponding to the low magnification image, for each candidate object of interest identified in (f);
   (i) automatically transforming pixels of the higher magnification image in a first color space to a second color space to differentiate higher magnification candidate object of interest pixels from background pixels;
   (j) automatically identifying, at high magnification, an object of interest from the candidate object of interest pixels in the second color space; and
   (k) automatically determining the optical density of the protein in a cell contained in a subsample, wherein the optical density is indicative of the residual component of a cellular protein.

2. The method of claim 1, wherein the first color space comprises red, green, and blue components for each pixel and the transforming step includes converting the red, blue and green components for each pixel in the first color space to pixel values in a hue, saturation, and intensity space.

3. The method of claim 2, wherein the hue, saturation, and intensity pixel values are compared to a threshold to identify pixels having a component value equal to or greater than said threshold as candidate object of interests pixels.

4. The method of claim 1, wherein the cellular protein is an enzyme.

5. The method of claim 4, wherein the enzyme is alkaline phosphatase (AP).

6. The method of claim 4, wherein the enzyme is acid phosphatase (AcP).

7. The method of claim 4, wherein the enzyme is "-naphthyl butyrate esterase.

8. The method of claim 1, wherein the cellular protein is assayed immunologically.

9. The method of claim 1, wherein the image is a color image.

10. The method of claim 1, wherein the image is a digital image.

11. A computer program, residing on a computer-readable medium, for obtaining images of subsamples of a cellular specimen, the computer program comprising instructions for causing a computer to:
   (a) select a Z position for imaging a candidate object of interest in a subsample;
   (b) obtain a low magnification image of the candidate object of interest comprising obtaining a plurality of pixels;
   (c) filter the candidate object of interest pixels in each subsample with a low pass filter;
   (d) morphologically process the candidate object of interest pixels in each subsample to identify artifact pixels;
   (e) identify the candidate object of interest by eliminating pixels identified as artifact pixels;
   (f) adjust the apparatus to a higher magnification;
   (g) acquire a higher magnification image of the subsample, at the location coordinates corresponding to the low magnification image, for each candidate object of interest identified in (e);
   (h) transform pixels of the higher magnification image in a first color space to a second color space to differentiate higher magnification candidate object of interest pixels from background pixels;

(i) identify, at higher magnification, an object of interest from the candidate object of interest pixels in the second color space; and (j) score a protein level in the subsample by determining the optical density of the protein in a cell.

12. An automated method for the measurement of residual protein in a cellular specimen, comprising:

(a) providing a plurality of stained subsamples from a cellular specimen;

(b) automatically selecting a Z position in each subsample for imaging a candidate object of interest;

(c) automatically obtaining a low magnification image of the candidate objects of interest comprising obtaining a plurality of pixels in each subsample;

(d) automatically filtering the candidate object of interest pixels in each subsample with a low pass filter;

(e) automatically morphologically processing the candidate object of interest pixels in each subsample to identify artifact pixels;

(f) automatically identifying the candidate object of interest in each subsample by eliminating pixels identified as artifact pixels;

(g) adjusting the apparatus to a higher magnification;

(h) automatically acquiring a higher magnification image of the subsample, at the location coordinates corresponding to the low magnification image, for each candidate object of interest identified in (f);

(i) automatically transforming pixels of the higher magnification image in a first color space to a second color space to differentiate higher magnification candidate object of interest pixels from background pixels;

(j) automatically identifying, at high magnification, an object of interest from the candidate object of interest pixels in the second color space; and (k) automatically identifying cells contained in a subsample and automatically determining the optical density of the protein in a cell contained in an identified cell, wherein the optical density is indicative of the residual component of a cellular protein.

* * * * *